US011111339B2

(12) United States Patent
Dussaud et al.

(10) Patent No.: US 11,111,339 B2
(45) Date of Patent: Sep. 7, 2021

(54) POLYACRYLATE SALT, METHODS OF PREPARATION AND APPLICATIONS FOR EMPLOYING THE SAME

(71) Applicant: Momentive Performance Materials Inc., Waterford, NY (US)

(72) Inventors: Anne Dussaud, Tarrytown, NY (US); Ning Lu, Chappaqua, NY (US); Bhavna Rana, White Plains, NY (US); Sigfredo Gonzalez, Danbury, CT (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 14/959,308

(22) Filed: Dec. 4, 2015

(65) Prior Publication Data

US 2017/0158823 A1 Jun. 8, 2017

(51) Int. Cl.
| | | |
|---|---|---|
| *A61K 8/81* | (2006.01) | |
| *C08G 77/445* | (2006.01) | |
| *C08G 77/442* | (2006.01) | |
| *A61K 8/41* | (2006.01) | |
| *C08L 33/02* | (2006.01) | |
| *C08L 33/08* | (2006.01) | |
| *A61Q 19/00* | (2006.01) | |
| *C08L 83/10* | (2006.01) | |
| *C08L 33/06* | (2006.01) | |
| *A61K 8/898* | (2006.01) | |
| *A61Q 5/00* | (2006.01) | |
| *A61Q 5/06* | (2006.01) | |
| *A61Q 17/04* | (2006.01) | |

(52) U.S. Cl.
CPC .............. *C08G 77/445* (2013.01); *A61K 8/41* (2013.01); *A61K 8/8141* (2013.01); *A61K 8/8147* (2013.01); *A61K 8/898* (2013.01); *A61Q 5/00* (2013.01); *A61Q 5/06* (2013.01); *A61Q 17/04* (2013.01); *A61Q 19/007* (2013.01); *C08G 77/442* (2013.01); *C08L 33/02* (2013.01); *C08L 33/06* (2013.01); *C08L 33/08* (2013.01); *C08L 83/10* (2013.01); *A61K 2800/48* (2013.01); *A61K 2800/548* (2013.01)

(58) Field of Classification Search
CPC ..... A61K 8/8141; A61K 8/8147; A61K 8/898
See application file for complete search history.

(56) References Cited

U.S. PATENT DOCUMENTS

| | | | |
|---|---|---|---|
| 2,340,110 A | 1/1944 | D'Alello | |
| 2,340,111 A | 1/1944 | D'Alello | |
| 2,533,635 A | 12/1950 | Seymour | |
| 2,798,053 A | 7/1957 | Brown | |
| 3,940,351 A | 2/1976 | Schlatzer, Jr. | |
| 4,062,817 A | 12/1977 | Westerman | |
| 5,034,486 A | 7/1991 | Tzai et al. | |
| 5,034,487 A | 7/1991 | Tazi et al. | |
| 5,034,488 A | 7/1991 | Tazi et al. | |
| 5,648,083 A * | 7/1997 | Blieszner | A61K 8/0208 424/402 |
| 6,225,467 B1 | 5/2001 | Esteghamatian et al. | |
| 6,475,568 B1 | 11/2002 | Czech | |
| 7,851,548 B2 | 12/2010 | Anyanwu et al. | |
| 8,742,152 B2 | 6/2014 | Yaghi et al. | |
| 9,243,142 B2 | 1/2016 | Dussaud et al. | |
| 2011/0105406 A1* | 5/2011 | Li | A61K 8/4926 514/18.8 |
| 2013/0121948 A1 | 5/2013 | Dussaud et al. | |
| 2014/0045949 A1 | 2/2014 | Goutayer et al. | |

FOREIGN PATENT DOCUMENTS

| | | |
|---|---|---|
| DE | 10200709647 | 8/2008 |
| WO | 02051828 | 7/2002 |
| WO | 2004055081 | 7/2004 |
| WO | 2004085412 | 10/2004 |
| WO | 2006034982 | 4/2006 |
| WO | 2006034985 | 4/2006 |
| WO | 2006034991 | 4/2006 |
| WO | 2006034992 | 4/2006 |
| WO | 2006035000 | 4/2006 |
| WO | 2006035007 | 4/2006 |
| WO | 2013074912 | 5/2013 |

OTHER PUBLICATIONS

International Search Report and Written Opinion from PCT/US2016/064323 dated Feb. 24, 2017.

* cited by examiner

*Primary Examiner* — James W Rogers
(74) *Attorney, Agent, or Firm* — Joseph S. Ostroff

(57) ABSTRACT

The present invention relates to a crosslinked polyacrylate salt, which has been neutralized by two types of amines: (1) amine groups attached to the polymer backbone of an aminosilicone and (2) water soluble organic amines. The compositions of the present invention can readily swell in water, displaying enhanced thickening, emulsifying, dispersing and producing film with water resistance compared to acrylate based thickener alone. The compositions can be used to formulate a wide variety of ingredients, such as, for example, fatty substances, humectants, solid particles, silicones, organic or inorganic sunscreens, without the need of further neutralizing agents, dispersants or emulsifiers.

16 Claims, No Drawings

POLYACRYLATE SALT, METHODS OF PREPARATION AND APPLICATIONS FOR EMPLOYING THE SAME

FIELD OF INVENTION

The present invention relates to a crosslinked polyacrylate salt, which has been neutralized by two types of amines: (1) amine groups attached to the polymer backbone of an aminosilicone and (2) water soluble organic amines.

BACKGROUND OF THE INVENTION

Natural and synthetic thickeners are readily available and widely used in the art. A thickener may need to meet a broad range of requirements depending on the application. For example, a thickener may need to have a particular shear thinning behavior, low tack on drying, emulsifying property, or a particular thickening profile at elevated temperature.

Acrylate-based thickeners and other acid containing polymers derived from olefinically unsaturated polymerisable monomers have been tailored to cover a broad range of applications involving aqueous systems.

Aqueous thickeners are easy to use, do not require a neutralizing step, can disperse pigments well and emulsify a large amount of oils. The acrylate dispersions made by emulsion polymerization usually do not require a neutralization step, but they contain emulsifiers that impart poor water resistance to the film they form after drying. For personal care applications, there is a need for acrylate thickeners with good water resistance and for reducing the tack of acrylated thickeners.

Association product of an acrylate thickener and a specific aminosilicone copolymer with improved performance for personal care products are disclosed in U.S. Patent Publication 2013/0121948. In Publication '948, a non-covalent reaction product of an acrylate thickener and a specific aminosilicone was prepared by a method comprising 3 steps: step (i) blending the acrylate with the aminosilicone in non aqueous medium at the temperature in the range of 30° C. to 200° C. for a period of about 1 min to about 120 minutes to produce a blend, step (ii) adding an aqueous base to the blend made from step (i) at the temperature in the range of 30° C. to 95° C. to produce a mixture, and step (iii) cooling the mixture obtained from step (ii) to provide the non-covalent bonded reaction product. Stable paste compositions (Example 25-27) provide good thickening when diluted with water but they were not practical because of their very long preparation time and their pasty texture. In addition, compositions prepared using a non-aqueous condition in step (i) cannot thicken well with water.

SUMMARY OF THE INVENTION

The present invention provides compositions comprising a crosslinked polyacrylate salt, which has been neutralized by two types of amines: an amine attached to the polymer backbone of a specific aminosilicone and a water soluble organic amine.

Surprisingly, an improved composition was found by reacting the acrylate thickener with the aminosilicone copolymers in the presence of a reaction-promoting amount of water and at the temperature between 50° C. and 120° C. The compositions are easy to use because of their soft texture and good thickening property in water. The film obtained from these compositions is highly water resistant.

Moreover, the compositions can be used to formulate a wide variety of ingredients, such as, for example, fatty substances, humectants, solid particles, silicones, organic or inorganic sunscreens, without the need of further neutralizing agents, dispersants or emulsifiers.

The compositions of the present invention can readily swell in water, displaying enhanced thickening, emulsifying, dispersing and producing film with water resistance compared to acrylate based thickener alone. The low tack of the final aqueous emulsion is particularly useful in personal care applications.

In particular, the composition containing the crosslinked polyacrylate salt is obtained by the steps of (a) reacting a crosslinked polyacrylic polymer and an aminosilicone copolymer in the presence of a reaction-promoting amount of water and optionally a non-aqueous diluent, to obtain an intermediate wax composition; and (b) reacting the intermediate wax composition with an aqueous solution of an organic amine base solution to produce the crosslinked polyacrylate salt having a Brookfield viscosity at 25° C. in the range of 5,000 to 100,000 cp when diluted at 3 wt % in water, more specifically from 10,000 to 70,000 cp, and most specifically from 15,000 to 50,000 cp.

The backbone of the crosslinked polyacrylate salt of the present invention is represented by the general formula:

$$-[CH_2-CR]_x-[CH_2-CR]_y-[CH_2-CR]_z-$$
$$\quad\ \ \ |\quad\quad\quad\ \ \ |\quad\quad\quad\ \ \ |$$
$$\quad\ \ COO^\ominus X^\oplus\ \ COO^\ominus Y^\oplus\ \ COOR'$$

wherein

R is selected from the group consisting of hydrogen, alkyl group, aryl group, alkaryl/aralkyl groups, and cycloaliphatic groups, R' is selected from the group consisting of alkyl group, aryl group and alkyl/aryl groups having from 1 to 30 carbon atoms, $X^\oplus$ is a cationic amine group of the aminosilicone copolymer, $Y^\oplus$ is a cationic amine group of the organic amine base, x is an integer between 50 and 20,000;

y is an integer between 50 and 20,000;

z is an integer between 0 and 5,000; and, the ratio of x:(x+y) is between 0.02 and 0.2, wherein the aminosilicone copolymer is selected from the group consisting of (i) an aminosilicone copolymer resulting from the reaction of:

$R^1R^2NH$ and wherein $R^1$ is $R^3(OC_aH_{2a})_m-$, $R^2$ is selected from the group consisting of H and $R^4(OC_cH_{2c})_o-$, $R^3$ is $(C_nH_{2n+1})$— where n is an integer from 1 to 30, or $(C_nH_{2n'-1})$— where n' is an integer from 2 to 30, or $(C_{n''}H_{2n''-3})$— where n" is an integer from 4 to 30, $R^4$ is $(C_qH_{2q+1})$— where q is an integer from 1 to 30, or $(C_qH_{2q'-1})$— where q' is an integer from 2 to 30, or $(C_{q''}H_{2q''-3})$— where q" is an integer from 4 to 30, a is an integer from 2 to 4,
m is 0 or an integer from 1 to 200,
c is an integer from 2 to 4,
o is 0 or an integer from 1 to 200, and
p is an integer from 2 to 1,000;

(ii) a block copolymer having the general formula of [AB]n wherein

A is a polysiloxane group having the general formula of $$[X(C_aH_{2a}O)_bR^6[(SiO(R^5)_2]_cSi(R^5)_2R^6(OC_aH_{2a})_bX],$$

B is a polyalkyleneoxide group having the general formula of $$[YO(C_aH_{2a}O)_dY],$$

$R^5$ is an alkyl containing from 1 to 4 carbon atoms,
$R^6$ is a divalent organic moiety,
X and Y are divalent organic groups selected from a secondary or tertiary amine and a ring opened epoxide, such that when X is a ring opened epoxide, Y is an amine and vice versa,
a is independently 2 to 4,
b is independently 0 to 100,
c is 1 to 500,
d is 0 to 100, and
(b+d) is 1 to 100; and, (iii) a random copolymer of C and D
wherein
C is a polysiloxane group having the general formula:

$$-CR^7R^8-CR^9(OH)R^{11}-(SiR^{10}_2O)_x-SiR^{10}_2-R^{11}CR^9(OH)CR^7R^8-L-$$

wherein
$R^7$ is independently selected from the group consisting of hydrogen and alkyl, aryl, alkenyl, or aralkyl group containing up to 20 carbon atoms, and optionally containing an oxygen atom, $R^8$ is independently selected from the group consisting of a hydrogen and an alkyl, aryl, alkenyl, or aralkyl group containing up to 20 carbon atoms, and optionally containing an oxygen atom, $R^9$ is independently selected from the group consisting of hydrogen, and an alkyl, aryl, alkenyl, or aralkyl group containing up to 20 carbon atoms, and optionally containing an oxygen atom, with the proviso that if $R^8$ is a chemical bond, then $R^9$ is a divalent hydrocarbon group of from 1 to 20 carbon atoms, and optionally containing an oxygen atom, that form a ring containing the chemical bond, $R^8$, $R^{10}$ is independently selected from the group consisting of hydrogen, and an alkyl, alkenyl, aryl or aralkyl group containing up to 10 carbon atoms, $R^{11}$ is a divalent hydrocarbon radical containing from 1 to 20 carbon atoms, and optionally containing an oxygen atom, L is independently a divalent linking group selected from the group consisting of
—$N(R^{12}NR^{13}_2)$— and $$-N-R^{12}-N\bigcirc R^{14}$$

wherein
$R^{12}$ is a divalent hydrocarbon radical containing from 1 to 20 carbon atoms,
$R^{13}$ is independently hydrocarbon radical containing from 1 to 20 carbon atoms, and
$R^{14}$ is a divalent hydrocarbon group containing from 2 to 20 carbon atoms, and optionally containing an oxygen atom or an —$NR^{13}$— group,
x is an integer from 1 to 500, and
D is a polyalkylene oxide having the general formula of $$-CR^7R^8-CR^9(OH)R^{11}-O(C_aH_{2a}O)_bR^{11}C-R^9(OH)CR^7R^8-L-$$

wherein $R^7$, $R^8$, $R^9$, $R^{11}$, L, a and b are defined as above.

The present invention is further described in the detailed description section provided below.

DETAILED DESCRIPTION OF THE INVENTION

It has been unexpectedly discovered by the inventors herein:
(i) that the neutralized crosslinked polyacrylic polymers of the present invention swells immediately in water;
(ii) that the neutralized crosslinked polyacrylic polymers of the present invention help emulsify and stabilize organic and silicone oils and mineral oils and sunscreen oils in aqueous emulsions without the need of additional emulsifiers;
(iii) that the neutralized crosslinked polyacrylic polymers of the present invention help disperse and stabilize inorganic pigments without the need of additional dispersants;
(iv) that the neutralized crosslinked polyacrylic polymers of the present invention produced film with water resistance useful in sunscreen applications or color cosmetics; and
(v) that the neutralized crosslinked polyacrylic polymers of the present invention is useful in industrial applications involving thickening of aqueous phase such as the textile industry, oil extraction, coating, paints, agriculture, emulsification and the personal care industry.

In the specification and claims herein, the following terms and expressions are to be understood as indicated.

As used in the specification and including the appended claims, the singular forms "a," "an," and "the" include the plural, and reference to a particular numerical value includes at least that particular value, unless the context clearly dictates otherwise.

Ranges expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising", "including," "containing," "characterized by," and grammatical equivalents thereof are inclusive or open-ended terms that do not exclude additional, unrecited elements or method steps, but will also be understood to include the more restrictive expressions "consisting of" and "consisting essentially of." The expression "consisting essentially of" limits the scope of a claim to the specified materials or steps and those that do not materially affect the basic and novel characteristics of the claimed invention. The expression "consisting of" excludes any element, step, or ingredient not specified in the claim.

Other than in the working examples or where otherwise indicated, all numbers expressing amounts of materials, reaction conditions, time durations, quantified properties of materials, and so forth, stated in the specification and claims are to be understood as being modified in all instances by the term "about."

It will be understood that any numerical range recited herein includes all subranges within that range and any combination of the various endpoints of such ranges or subranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The expression "aliphatic hydrocarbon" means any hydrocarbon group from which one or more hydrogen atoms has been removed and is inclusive of alkyl, alkenyl, alkynyl, cyclic alkyl, cyclic alkenyl, cyclic alkynyl, aryl, aralkyl and arenyl and may contain heteroatoms.

The term "alkyl" means any monovalent, saturated straight, branched or cyclic hydrocarbon group; the teen "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

The expressions "cyclic alkyl", "cyclic alkenyl", and "cyclic alkynyl" include bicyclic, tricyclic and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, cyclohexyl, ethylcyclohexyl, ethylcyclohexenyl, cyclohexylcyclohexyl and cyclododecatrienyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

It will be understood herein that all measures of viscosity are obtained at 25° C. unless noted otherwise.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Examples of useful monovalent hydrocarbon radicals for the silicones described herein include those independently selected from the group consisting of methyl, ethyl, n-propyl, iso-propyl, n-butyl, isobutyl, tert-butyl, n-pentyl, iso-pentyl, neopentyl, tert-pentyl, hexyl, such as the n-hexyl group, heptyl, such as the n-heptyl group, octyl, such as the n-octyl snf isooctyl groups, 2,2,4-trimethylpentyl, nonyl, such as the n-nonyl group, decyl, such as the n-decyl group, cycloalkyl radicals, such as cyclopentyl, cyclohexyl, cycloheptyl and methylcyclohexyl, and aryl groups such as phenyl, naphthyl; o-, m- and p-tolyl, xylyl, ethylphenyl, and benzyl.

Polyacrylic Polymers

The polyacrylic polymers, such as homopolymers or copolymers, contain acrylic acid monomers and optionally nonionic monomers or cationic monomers. Typical materials are those described in U.S. Pat. No. 2,798,053, the contents of which are incorporated by reference herein. Copolymers, for example, include copolymers of acrylic acid with small amounts of polyalkenyl polyether cross-linkers that are gel-like polymers, which, especially in the form of their salts, absorb large quantities of water or solvents with subsequent substantial increase in volume. Other useful carboxyl containing polymers are described in U.S. Pat. No. 3,940,351, directed to polymers of unsaturated carboxylic acid and at least one alkyl acrylic or methacrylic ester where the alkyl group contains 10 to 30 carbon atoms, and U.S. Pat. Nos. 5,034,486; 5,034,487; and 5,034,488; which are directed to maleic anhydride copolymers with vinyl ethers. Other types of such copolymers are described in U.S. Pat. No. 4,062,817 wherein the polymers described in U.S. Pat. No. 3,940,351 contain additionally another alkyl acrylic or methacrylic ester and the alkyl groups contain 1 to 8 carbon atoms. Carboxylic polymers and copolymers such as those of acrylic acid and methacrylic acid also may be cross-linked with polyfunctional materials as divinyl benzene, unsaturated diesters and the like, as is disclosed in U.S. Pat. Nos. 2,340,110; 2,340,111; and 2,533,635. The contents of above patents are incorporated by reference herein.

The carboxylic acid containing polymers are prepared from monomers containing at least one activated >C=C< group and a carboxyl group. Such polymers are homopolymers of an unsaturated, polymerizable carboxylic monomers such as acrylic acid, methacrylic acid, maleic acid, itaconic acid, maleic anhydride, and the like, and copolymers of polymerizable carboxylic monomers with acrylate/methacrylate esters, acrylamides, olefins, vinyl esters, vinyl ethers, or styrenics. The carboxylic acid containing polymers have molecular weights greater than about 500 to as high as several million, usually greater than about 10,000 to 900,000 or more. The carboxylic monomers are the olefinically-unsaturated carboxylic acids containing at least one activated carbon-to-carbon olefinic double bond, and at least one carboxyl group. Olefinically-unsaturated acids of this class include such materials as the acrylic acids typified by the acrylic acid itself, alpha-cyano acrylic acid, beta methylacrylic acid (crotonic acid), alpha-phenyl acrylic acid, beta-acryloxy propionic acid, cinnamic acid, p-chloro cinnamic acid, 1-carboxy-4-phenyl butadiene-1,3, itaconic acid, citraconic acid, mesaconic acid, glutaconic acid, aconitic acid, maleic acid, fumaric acid, and tricarboxy ethylene. As used herein, the term "carboxylic acid" includes the polycarboxylic acids and those acid anhydrides, such as maleic anhydride, wherein the anhydride group is formed by the elimination of one molecule of water from two carboxyl groups located on the same carboxylic acid molecule. Maleic anhydride and other acid anhydrides are useful herein. The preferred carboxylic monomers are the monoolefinic acrylic acids acrylic and methacrylic acid. Other useful carboxylic monomers are maleic acid and its anhydride. The polymers include both homopolymers of carboxylic acids or anhydrides thereof, or the defined carboxylic acids copolymerized with one or more other vinylidene monomers containing at least one terminal

group.

Such monomers include, for example, acrylate ester monomers including those acrylic acid ester monomers. Representative acrylates include methyl acrylate, ethyl acrylate, propyl acrylate, isopropyl acrylate, butyl acrylate, isobutyl acrylate, methyl methacrylate, methyl ethacrylate, ethyl methacrylate, octyl acrylate, heptyl acrylate, octyl methacrylate, isopropyl methacrylate, 2-ethylhexyl methacrylate, nonyl acrylate, hexyl acrylate, n-hexyl methacrylate, and the like. Higher alkyl acrylic esters are decyl acrylate, isodecyl methacrylate, lauryl acrylate, stearyl acrylate, behenyl acrylate and melissyl acrylate. Mixtures of two or three or more long chain acrylic esters may be successfully polymerized with one of the carboxylic monomers. Other comonomers include olefins, including alpha olefins, vinyl ethers, vinyl esters, and mixtures thereof.

The hydrophilic polymers also may be the kinds which are cross-linked with any polyene, e.g. decadiene or trivinyl cyclohexane; acrylamides, such as methylene bis acrylamide; polyfunctional acrylates, such as trimethylol propane triacrylate; or polyfunctional vinylidene monomer containing at least 2 terminal

groups, including for example, butadiene, isoprene, divinyl benzene, divinyl naphthlene, allyl acrylates and the like. Particularly useful cross-linking monomers for use in preparing the copolymers are polyalkenyl polyethers having more than one alkenyl ether grouping per molecule. The most useful possess alkenyl groups in which an olefinic double bond is present attached to a terminal methylene grouping, $CH_2=C<$. They are made by the etherification of a polyhydric alcohol containing at least 2 carbon atoms and at least 2 hydroxyl groups.

Compounds of this class may be produced by reacting an alkenyl halide, such as allyl chloride or allyl bromide, with a strongly alkaline aqueous solution of one or more polyhydric alcohols. The product may be a complex mixture of polyethers with varying numbers of ether groups. Analysis reveals the average number of ether groupings on each molecule. Efficiency of the polyether cross-linking agent increases with the number of potentially polymerizable groups on the molecule. It is preferred to utilize polyethers containing an average of two or more alkenyl ether groupings per molecule.

Other cross-linking monomers include, for example, diallyl esters, dimethallyl ethers, allyl or methallyl acrylates and acrylamides, tetraallyl tin, tetravinyl silane, polyalkenyl methanes, diacrylates, and dimethacrylates, divinyl compounds such as divinyl benzene, polyallyl phosphate, diallyloxy compounds and phosphite esters and the like. Typical agents are allyl pentaerythritol, allyl sucrose, trimethylolpropane triacrylate, 1,6-hexanediol diacrylate, trimethylolpropane diallyl ether, pentaerythritol triacrylate, tetramethylene dimethacrylate, ethylene diacrylate, ethylene dimethacrylate, triethylene glycol dimethacrylate, and the like. Some such suitable crosslinked commercial polyacrylic polymers are carbopols such as carbopol 980, carbopol 1382, Ultrez 10 available from Lubrizol. Other examples are Ashland 981 carbomers, Ashland 980 carbomers, carbomers available commercially from 3V Inc. under the trademark Polygel (Polygel HP, Polymer W30, Polygel DV).

Aminosilicone Copolymers

Suitable aminosilicone copolymers for the present invention are described in U.S. Pat. Nos. 8,742,154, 6,475,568 and U.S. Pat. No. 7,851,548, the contents of which are incorporated by references herein.

The cationic amine group $X^\oplus$ is attached to an aminosilicone copolymer selected from the group consisting of
(i) an aminosilicone copolymer resulting from the reaction of:
$R^1R^2NH$ and

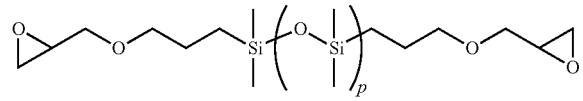

wherein
$R^1$ is $R^3(OC_aH_{2a})_m-$,
$R^2$ is selected from the group consisting of H and $R^4(OC_cH_{2c})_o-$,
$R^3$ is $(C_nH_{2n+1})-$ where n is an integer from 1 to 30, or $(C_{n'}H_{2n'-1})-$ where n' is an integer from 2 to 30, or $(C_{n''}H_{2n''-3})-$ where n" is an integer from 4 to 30,
$R^4$ is $(C_qH_{2q+1})-$ where q is an integer from 1 to 30, or $(C_{q'}H_{2q'-1})-$ where q' is an integer from 2 to 30, or $(C_{q''}H_{2q''-3})-$ where q" is an integer from 4 to 30,
a is an integer from 2 to 4,
m is 0 or an integer from 1 to 200,
c is an integer from 2 to 4,
o is 0 or an integer from 1 to 200, and
p is an integer from 2 to 1,000;

(ii) a block copolymer having the general formula of [AB]n wherein

A is a polysiloxane group having the general formula of

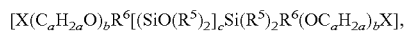
$[X(C_aH_{2a}O)_bR^6[(SiO(R^5)_2]_cSi(R^5)_2R^6(OC_aH_{2a})_bX]$,

B is a polyalkyleneoxide group having the general formula of

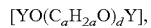
$[YO(C_aH_{2a}O)_dY]$, $R^5$ is an alkyl containing from 1 to 4 carbon atoms, $R^6$ is a divalent organic moiety, X and Y are divalent organic groups selected from a secondary or tertiary amine and a ring opened epoxide, such that when X is a ring opened epoxide, Y is an amine and vice versa, a is independently 2 to 4, b is independently 0 to 100, c is 1 to 500, d is 0 to 100, and (b+d) is 1 to 100; and, (iii) a random copolymer of C and D wherein C is a polysiloxane group having the general formula:

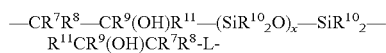
$-CR^7R^8-CR^9(OH)R^{11}-(SiR^{10}_2O)_x-SiR^{10}_2-R^{11}CR^9(OH)CR^7R^8-L-$ wherein $R^7$ is independently selected from the group consisting of hydrogen and alkyl, aryl, alkenyl, or aralkyl group containing up to 20 carbon atoms, and optionally containing an oxygen atom, $R^8$ is independently selected from the group consisting of a hydrogen and an alkyl, aryl, alkenyl, or aralkyl group containing up to 20 carbon atoms, and optionally containing an oxygen atom, $R^9$ is independently selected from the group consisting of hydrogen and an alkyl, aryl, alkenyl, or aralkyl group containing up to 20 carbon atoms, and optionally containing an oxygen atom, with the proviso that if $R^8$ is a chemical bond, then $R^9$ is a divalent hydrocarbon group of from 1 to 20 carbon atoms, and optionally containing an oxygen atom, that form a ring containing the chemical bond, $R^8$, $R^{10}$ is independently selected from the group consisting of hydrogen, and an alkyl, alkenyl, aryl or aralkyl group containing up to 10 carbon atoms, $R^{11}$ is a divalent hydrocarbon radical containing from 1 to 20 carbon atoms, and optionally containing an oxygen atom, L is independently a divalent linking group selected from the group consisting of

$-N(R^{12}NR^{13}_2)-$ and

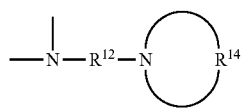

wherein $R^{12}$ is a divalent hydrocarbon radical containing from 1 to 20 carbon atoms, $R^{13}$ is independently hydrocarbon radical containing from 1 to 20 carbon atoms, and $R^{14}$ is a divalent hydrocarbon group containing from 2 to 20 carbon atoms, and optionally containing an oxygen atom or an $-NR^{13}-$ group, x is an integer from 1 to 500, and D is a polyalkylene oxide having the general formula of

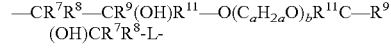
$-CR^7R^8-CR^9(OH)R^{11}-O(C_aH_{2a}O)_bR^{11}C-R^9(OH)CR^7R^8-L-$ wherein $R^7$, $R^8$, $R^9$, $R^{11}$, L, a and b are defined as above.

An aminosilicone copolymer is, for example, a non-hydrolyzable, random block polysiloxane, polyalkyleneoxide copolymer linked by a bis-aminofunctional group, which on one end forms a tertiary amine linkage between the monomers within the polymer chain and the other end resides as a pendant amino-functional group. One example of such is a non-hydrolyzable, random blocked polysiloxane-polyalkylene oxide composition having the general Formula:

$$E^1[A]_m[B]_nE^2 \qquad (I)$$

wherein each A is independently a polysiloxane unit of structure  $-CR^1R^2-CR^3(OH)R^5-(SiR^4_2O)_x-SiR^4_2-R^5CR^3(OH)CR^1R^2-L-$ wherein each $R^1$ is selected independently from the group consisting of a hydrogen, and an alkyl, aryl, alkenyl, and aralkyl containing from 1 to 20 carbon atoms and optionally contains an oxygen atom; each $R^2$ is selected independently from the group consisting of a hydrogen and an alkyl, aryl, alkenyl, and aralkyl containing from 1 to 20 carbon atoms and optionally contains an oxygen atom; each $R^3$ is selected independently from the group consisting of a hydrogen, an alkyl, aryl, alkenyl, and aralkyl containing from 1 to 20 carbon atoms and optionally contains an oxygen atom, with the proviso that if $R^2$ is a chemical bond, then $R^3$ is a divalent hydrocarbon of 1 to 20 carbon atoms and optionally contains an oxygen atom that form a ring containing the chemical bond, $R^2$; each $R^4$ is independently selected from the group consisting of hydrogen, and an alkyl, alkenyl, aryl or aralkyl group containing 1 to 10 carbon atoms; each $R^5$ is a divalent hydrocarbon radical containing from 1 to 20 carbon atoms and optionally containing an oxygen atom; each L is independently a divalent linking group selected from the group consisting of $-N(R^6NR^7_2)-$, and

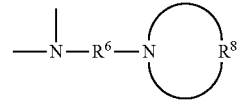

wherein each $R^6$ is a divalent hydrocarbon radical containing from 1 to 20 carbon atom, each $R^7$ is an independently monovalent hydrocarbon radical containing from 1 to 20 carbon atoms and $R^8$ is a divalent hydrocarbon of containing 2 to 20 carbon atoms and optionally contains an oxygen atom or an $-NR^7-$ group; and x is an integer from 1 to 500;

each B is independently a polyalkylene oxide unit of structure $-CR^1R^2-CR^3(OH)R^5-O(C_aH_{2a}O)_bR^5C-R^3(OH)CR^1R^2-L-$ wherein each $R^1$ is selected independently from the group consisting of a hydrogen, and an alkyl, aryl, alkenyl, and aralkyl containing from 1 to 20 carbon atoms and optionally contain an oxygen atom; each $R^2$ is selected independently from the group consisting of a hydrogen and an alkyl, aryl, alkenyl, and aralkyl containing from 1 to 20 carbon atoms and optionally contain an oxygen atom; each $R^3$ is selected independently from the group consisting of a hydrogen, an alkyl, aryl, alkenyl, and aralkyl containing from 1 to 20 carbon atoms and optionally contain an oxygen atom, with the proviso that if $R^2$ is a chemical bond, then $R^3$ is a divalent hydrocarbon of 1 to 20 carbon atoms and optionally contains an oxygen atom that form a ring containing the chemical bond, $R^2$; each $R^5$ is a divalent hydrocarbon radical containing from 1 to 20 carbon atoms and optionally containing an oxygen atom; each L is independently a divalent linking group selected from the group consisting of —N($R^6$N$R^7{}_2$)—, and

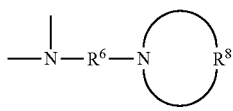

wherein each $R^6$ is a divalent hydrocarbon radical containing from 1 to 20 carbon atom, each $R^7$ is an independently monovalent hydrocarbon radical containing from 1 to 20 carbon atoms and $R^8$ is a divalent hydrocarbon of containing 2 to 20 carbon atoms and optionally contains an oxygen atom or an —N$R^7$— group; and x is an integer from 1 to 500;

each $E^1$ is a monovalent end-group independently selected from the group consisting of,

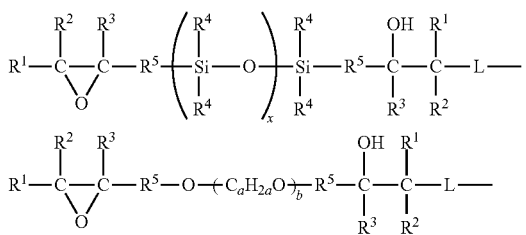

and H-L; and each $E^2$ is a monovalent end-group independently selected from the group consisting of hydrogen,

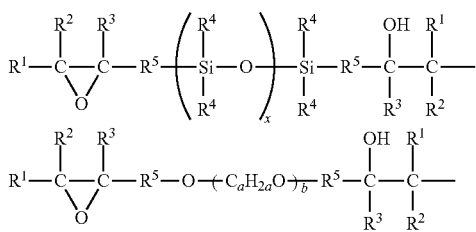

each m and n is independently an integer from 1 to 500, and a is from 2 to 4, b is from 2 to 100, and preferably 3 to 50 and where $R^1$, $R^2$, $R^3$, $R^4$ and $R^5$ are each independently as defined above.

One other example of copolymers (iii) which can be the hydrophobic polymer which contains an amine group directly bound to the hydrophobic polymer backbone described above can have in their structure polysiloxane units $\{XR^2[(SiO(R^1)_2]_xSi(R^1)_2R^2X\}$, polyalkyleneoxide units $\{YO(C_aH_{2a}O)_bY\}$ and linking groups —N$R^3$—, wherein $R^1$ is alkyl, $R^2$ is a divalent organic moiety, X and Y are divalent organic groups formed by the ring opening of an epoxide, $R^3$ is selected from the group consisting of alkyl, alkenyl, aryl, aralkyl, oxygen-containing alkyl, oxygen-containing aryl, and oxygen-containing aralkyl, a is 2 to 4, b is 2 to 100, preferably 3 to 50, x is 1 to 500, preferably 140 to 160.

$R^1$ is preferably lower alkyl, e.g., an alkyl having from one to four carbon atoms, i.e., methyl, ethyl, propyl, butyl, and isomers of the foregoing, e.g., isopropyl, t-butyl, and the like. More preferably, $R^1$ is methyl.

$R^2$ is preferably a divalent hydrocarbon group with at least one carbon, which may have hydroxy substitutions thereon and/or include an ether linkage. Preferably, it contains less than ten carbon atoms. Within a particular molecule, each $R^1$, $R^2$, $R^3$ and $R^4$ may be the same or different.

The copolymers are preferably end-capped with secondary amino groups —NH$R^3$ or tertiary groups —N$R^3R^4$, where $R^3$ is as defined above for linking groups —N$R^3$— and $R^4$ is also chosen from the group consisting of alkyl, alkenyl, aryl, aralkyl, oxygen-containing alkyl, oxygen-containing aryl, and oxygen-containing aralkyl, and where $R^3$ and $R^4$ can be the same or different.

The moieties comprising $R^3$ and $R^4$ preferably comprise from one to about twenty carbon atoms, e.g., methyl, ethyl, propyl, butyl, pentyl, hexyl, heptyl, octyl, nonyl, decyl, undecyl, oleyl, dodecyl, tridecyl, tetradecyl, pentadecyl, hexadecyl, heptadecyl, octadecyl, nonadecyl, eicosyl, methoxy, ethoxy, propoxy, butoxy, phenyl, biphenyl, naphthyl, tolyl, xylyl, anthracyl, methoxyphenyl, isomers of the foregoing, and the like.

Preferably the amine content of the aminosilicone copolymer is at least 0.08 meq/g.

Organic Amine Base

The organic amine base can be for example 2-amino-2methyl-1-propanol (AMP-95, AMP ultra PC2000), triethanolamine, tromethamine, L-arginine, triethanolamine, ethanolamine, diisopropanol amine, triisopropanol amine, tetrahydroxpropyl ethylene diamine, for example Neutrol TE from BASF and mixtures of organic amine bases.

The backbone of the crosslinked polyacrylate salt of the present invention is represented by the formula:

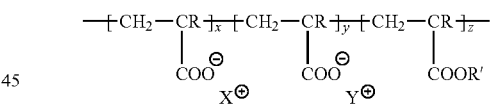

wherein

R is selected from the group consisting of hydrogen, alkyl group, aryl group, alkyl/aryl groups, and cycloaliphatic groups, R' is selected from the group consisting of alkyl group, aryl group and alkyl/aryl groups having from 1 to 30 carbon atoms, $X^\oplus$ is a cationic amine group of an aminosilicone copolymer, $Y^\oplus$ is a cationic amine of a water soluble organic amine base, x is an integer between 50 and 20,000, y is an integer between 50 and 20,000, z is an integer between 0 and 5,000, and the ratio of x:(x+y) is between 0.02 and 0.2.

Preparation Process

In one further embodiment there is provided a process of making a composition comprising the steps of:

1) reacting the crosslinked polyacrylic polymer with the aminosilicone copolymer in the presence of a reaction-promoting amount of water; and, optionally a non-aqueous diluent, to produce an intermediate wax composition; and 2) reacting the intermediate wax composition with an aqueous solution of an organic amine solution to produce a composition having a Brookfield viscosity from 5,000 to 100,000 cp when diluted at 3 wt % in water, more specifically from 10,000 to 70,000 cp, and most specifically from 15,000 to 50,000 cp.

In one embodiment herein the reaction-promoting amount of water used in step 1) is in the range of 0.2 to 10 wt %, more specifically from 0.3 to 5 wt %, most specifically from 0.5 to 3 wt %.

In one embodiment herein the reaction in step 1) is carried out at a temperature in the range of from 50° C. and 120° C., more specifically in the range of from 50° C. to 100° C.

In one embodiment herein the reaction in step 1) is carried out at a reaction time in the range of 1 to 12 hours, more specifically from 2 to 10 hours, and most specifically from 4 to 8 hours.

In one embodiment herein the optional diluents used herein can be low polarity oils and/or water. Low polarity oils need to be miscible with the hydrophobic polymer which contains an amine group bound directly to the hydrophobic polymer backbone and has a Hansen solubility parameter from about 12 $MPa^{0.5}$ to about 28 $MPa^{0.5}$, specifically from about 14 to about 20 $MPa^{0.5}$. Suitable oils include but are not limited to esters, mineral oils, silicone oils, triglycerides oils, fatty acids or combination of oils.

In one embodiment herein the neutralization in step 2) is carried out at a temperature in the range of 20 to 95° C., more specifically from 40 to 85° C.

In one embodiment herein the neutralization in step 2) is carried out over a period from 5 to 240 minutes, more specifically from 30 to 180 minutes, and most specifically from 60 to 120 minutes.

In one embodiment herein the base used in step 2) to provide the aqueous base solution is 2-amino-2-methyl-1-propanol (AMP) or tromethamine.

The composition of the present invention can contain antioxidants such as vitamin E, Tinogard TS from BASF or other suitable antioxidants.

Optional Ingredients

The composition of the present invention further contains the following optional ingredients.

Fatty Substances

The fatty substances may contain independently or in combination, oils and waxes. The term oil means a compound that is liquid at room temperature. The term wax means a compound that is solid or substantially solid at room temperature and whose melting point is generally greater than 35° C.

Examples of oils which can be used in the compositions of the present invention include polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, coconut oil, argan oil, jojoba oil, shea butter, cocoa butter, macadamia oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including and better still from 7 to 19 carbon atoms, and $R_6$ represents a branched hydrocarbon-based chain containing from 1 to 40 carbon atoms, including and better still from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol; and mixtures thereof.

Examples of fatty substances which can be used in the compositions of the present invention include non polar compounds such as: hydrocarbons, mineral oil, polyolefins such as polydecene, paraffins such as isohexadecane (e.g. Pennethyl 99® and Permethyl 101®), petrolatum, high molecular weight polybutenes.

Waxy compounds that are exemplary include carnauba wax, beeswax, ozokerite wax, candelilla wax, hydrogenated castor oil, polyethylene waxes and polymethylene waxes, for instance the product marketed under the trademark Cirebelle 303 by Sasol.

Organic Sunscreens

The organic screening agents are selected especially from among anthranilates; cinnamic derivatives; salicylic derivatives; camphor derivatives; benzophenone derivatives; β,β-diphenylacrylate derivatives; triazine derivatives; benzotriazole derivatives; benzalmalonate derivatives.

Examples of additional organic photoprotective agents include those indicated hereinbelow under their INCI name:

Cinnamic Derivatives:

Ethylhexyl methoxycinnamate marketed in particular under the trademark Parsol MCX by DSM Nutritional Products, Inc., Isopropyl methoxycinnamate, Isoamyl methoxycinnamate marketed under the trademark Neo Heliopan E 1000 by Symrise, Cinoxate, DEA methoxycinnamate, Diisopropyl methylcinnamate, Glyceryl ethylhexanoate dimethoxycinnamate.

Para-Aminobenzoic Acid Derivatives:

PABA,

Ethyl PABA,

Ethyl dihydroxypropyl PABA,

Ethylhexyl dimethyl PABA marketed in particular under the trademark Escalol 507 by ISP, Glyceryl PABA, PEG-25 PABA marketed under the trademark Uvinul P25 by BASF.

Salicylic Derivatives:

Homosalate marketed under the trademark Eusolex HMS by Rona/EM Industries,

Ethylhexyl salicylate marketed under the trademark Neo Heliopan OS by Symrise,

Dipropylene glycol salicylate marketed under the trademark Dipsal by Scher,
TEA salicylate marketed under the trademark Neo Heliopan TS by Symrise.

β,β-Diphenylacrylate Derivatives:

Octocrylene marketed in particular under the trademark Uvinul N539 by BASF,
Etocrylene marketed in particular under the trademark Uvinul N35 by BASF.

Benzophenone Derivatives:

Benzophenone-1 marketed under the trademark Uvinul 400 by BASF,
Benzophenone-2 marketed under the trademark Uvinul D50 by BASF,
Benzophenone-3 or Oxybenzone marketed under the trademark Uvinul M40 by BASF,
Benzophenone-4 marketed under the trademark Uvinul MS40 by BASF,
Benzophenone-5,
Benzophenone-6 marketed under the trademark Helisorb 11 by Norquay,
Benzophenone-8 marketed under the trademark SpectraSorb UV-24 by American Cyanamid,
Benzophenone-9 marketed under the trademark Uvinul DS-49 by BASF,
Benzophenone-12
n-hexyl 2-(4-diethylamino-2-hydroxybenzoyl)benzoate marketed under the trademark Uvinul A+ by BASF.

Benzylidenecamphor Derivatives:

3-Benzylidenecamphor manufactured under the trademark Mexoryl SD by Chimex,
4-Methylbenzylidenecamphor marketed under the trademark Eusolex 6300 by Merck,
Benzylidenecamphorsulfonic acid manufactured under the trademark Mexoryl SL by Chimex,
Camphor benzalkonium methosulfate manufactured under the trademark Mexoryl SO by Chimex,
Terephthalylidenedicamphorsulfonic acid manufactured under the trademark Mexoryl SX by Chimex,
Polyacrylamidomethylbenzylidenecamphor manufactured under the trademark Mexoryl SW by Chimex.

Phenylbenzimidazole Derivatives:

Phenylbenzimidazolesulfonic acid marketed in particular under the trademark Eusolex 232 by Merck,
Disodium phenyl dibenzimidazole tetrasulfonate marketed under the trademark Neo Heliopan AP by Symrise.

Phenylbenzotriazole Derivatives:

Drometrizole trisiloxane marketed under the trademark Silatrizole by Rhodia Chimie,
Methylenebis(benzotriazolyl)tetramethylbutylphenol marketed in solid form under the trademark MIXXIM BB/100 by Fairmount Chemical, or in micronized form as an aqueous dispersion under the trademark Tinosorb M by Ciba Specialty Chemicals.

Triazine Derivatives:

Bis(ethylhexyloxyphenol)methoxyphenyltriazine marketed under the trademark Tinosorb S by Ciba Geigy, Ethylhexyltriazone marketed in particular under the trademark Uvinul T150 by BASF,
Diethylhexylbutamidotriazone marketed under the trademark Uvasorb HEB by Sigma 3V,
2,4-bis(n-butyl 4'-aminobenzoate)-6-(aminopropyltrisiloxane)-s-triazine,
2,4,6-tris(dineopentyl 4'-aminobenzalmalonate)-s-triazine
2,4,6-tris(diisobutyl 4'-aminobenzalmalonate)-s-triazine,
1a 2,4bis(4'-aminobenzoate de n-butyle)-6-(aminopropyltrisiloxane)-s-triazine,
2,4-bis(dineopentyl 4'-aminobenzalmalonate)-6-(n-butyl 4'-aminobenzoate)-s-triazine,
the symmetrical triazine screening agents described in U.S. Pat. No. 6,225,467, WO 2004/085 412 (see compounds 6 and 9) or the document Symmetrical Triazine Derivatives IP.COM Journal, IP.COM INC West Henrietta, N.Y., US (20 Sep. 2004), especially 2,4,6-tris(biphenyl)-1,3,5-triazines (in particular 2,4,6-tris(biphenyl-4-yl-1,3,5-triazine) and 2,4,6-tris(terphenyl)-1,3,5-triazine which is also mentioned in WO 06/035 000, WO 06/034 982, WO 06/034 991, WO 06/035 007, WO 2006/034 992 and WO 2006/034 985.

Anthranilic Derivatives:

Menthyl anthranilate marketed under the trademark Neo Heliopan MA by Symrise.

Imidazoline Derivatives:

Ethylhexyldimethoxybenzylidenedioxoimidazoline propionate.

Benzalmalonate Derivatives:

Polyorganosiloxane containing benzalmalonate functions, for instance Polysilicone-15, marketed under the trademark Parsol SLX by DSM Nutritional products, Inc.

4,4-Diarylbutadiene Derivatives:

1,1-Dicarboxy(2,2'-dimethylpropyl)-4,4-diphenylbutadiene.

Benzoxazole Derivatives:

2,4-bis[5-(1-dimethylpropyl)benzoxazol-2-yl(4-phenyl)imino]-6-(2-ethylhexyl)i mino-1,3,5-triazine marketed under the trademark Uvasorb K2A by Sigma 3V.

Merocyanin Derivatives:

Octyl 5-N,N-diethylamino-2-phenylsulfonyl-2,4-pentadienoate, and mixtures thereof.

The preferred organic photoprotective agents are selected from among:
Ethylhexyl methoxycinnamate,
Ethylhexyl salicylate,
Homosalate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
Methylenebis(benzotriazolyl)tetramethylbutylphenol,
Bis(ethylhexyloxyphenol)methoxyphenyltriazine,
Ethylhexyltriazone,
Diethylhexylbutamidotriazone,
2,4-bis(4'-aminobenzoate of n-butyl)-6-(aminopropyltrisiloxane)-s-triazine,
2,4,6-Tris(dineopentyl 4'-aminobenzalmalonate)-s-triazine,
2,4,6-Tris(diisobutyl 4'-aminobenzalmalonate)-s-triazine,
2,4-Bis(dineopentyl 4'-aminobenzalmalonate)-6-(n-butyl 4'-aminobenzoate)-s-triazine,
2,4,6-Tris(biphenyl-4-yl)-1,3,5-triazine,
2,4,6-Tris(terphenyl)-1,3,5-triazine,
Drometrizole trisiloxane,
Polysilicone-15,
1,1-Dicarboxy(2,2'-dimethylpropyl)-4,4-diphenylbutadiene,
2,4-Bis[5-1(dimethylpropyl)benzoxazol-2-yl(4-phenyl)imino]-6-(2-ethylhexyl)imino-1,3,5-triazine,
Octyl 5-N,N-diethylamino-2-phenylsulfonyl-2,4-pentadienoate, and mixtures thereof.

Humectants

Suitable humectants include, but are not limited to polyhydric alcohols (polyols). Examples of polyhydric alcohols include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Most preferably the polyhydric alcohol is glycerin.

Other humectants or moisturizers include urea and derivatives thereof, especially Hydrovance® marketed by National Starch, lactic acid, hyaluronic acid, AHAs, BHAs, sodium pidolate, xylitol, serine, sodium lactate, ectoin and derivatives thereof, chitosan and derivatives thereof, collagen, plankton, an extract of *Imperata cylindra* marketed under the trademark Moist 24® by Sederma, acrylic acid homopolymers, for instance Lipidure-HM® from NOF Corporation, beta-glucan from Mibelle-AG-Biochemistry; a mixture of passionflower oil, apricot oil, corn oil and rice bran oil marketed by Nestlé under the trademark NutraLipids®; a C-glycoside derivative such as those described in WO 02/051 828 and in particular C-β-D-xylopyranoside-2-hydroxypropane in the form of a solution containing 30% by weight of active material in a water/propylene glycol mixture (60/40% by weight) such as the product marketed by Chimex under the trademark Mexoryl SBB®; an oil of musk rose marketed by Nestlé; an oil of the microalga *Prophyridium cruentum* enriched with zinc, marketed by Vincience under the trademark Algualane Zinc®; spheres of collagen and of chondroitin sulfate of marine origin (Atelocollagen) marketed by Engelhard Lyon under the trademark Marine Filling Spheres; hyaluronic acid spheres such as those marketed by Engelhard Lyon; and arginine.

Suitable moisturizers can also include sodium PCA and amino acid derived moisturizers, for examples the ingredients under the trademarks Prodew 500, Ajidew NL-50.

Silicones

The silicones can be linear polydimethylsiloxane polymers, dimethiconol polymers, alkyl silicones, silicone quats, phenyl modified silicones, aminofunctional silicones, aminofunctional silicones emulsions, silicone gum, silicone crosspolymer network, silicone resins (T resin or Q resin) silicone waxes. Examples of silicone polymers include the polymers from Momentive: aminosilicones under the trademarks Silsoft AX, Silsoft AX-E, SF1708, Silsoft A+, silicone waxes under the tradename SF1632, SF1642, the silicone resins under the trademarks Silform Flexible, SR1000, SS4230, SS4267, Silform FR-5, Silform FR-10, Silsoft Style, the silicone gels under the trademarks Velvesil 034, Velvesil FX, Velvesil Plus, Velvesil DM, Silsoft silicone gel, SFES39, the silicone gums under the trademark Silsoft1215, SF1236, CF1251, the silicone quats under the trademarks, silsoft Q, Silsoft Silk, the alkyl silicone under the trademark Silsoft ETS, Silsoft 034.

Silicone elastomers useful in accordance with the invention include, without limitation, compounds generally known as polyorganosiloxanes. The elastomers are by definition crosslinked, the degree of which can be vary depending on the elastic properties of the polymer that are desired. Cross-linking materials may be hydrophilic (ethylene oxide and propylene oxide, for example), hydrophobic (dimethicone, vinyl dimethicone, alkyl, etc.) or combinations thereof.

The silicone elastomers are typically dissolved in a suitable solvent, either prior to their introduction into the composition of the invention, or in situ within the composition. Examples of suitable solvents, include, but are not limited to, volatile and non-volatile silicones, volatile and non-volatile alcohols, volatile and non-volatile esters, volatile and non-volatile hydrocarbons and mixtures thereof. Preferred silicone elastomers for use herein are elastomer/solvent blends, also referred to as "gels", having an elastomer to solvent ratio from about 1:100 to about 1:1, more preferably from about 1:50 to about 1:5. Preferably the silicone elastomer/solvent blend has a viscosity of no more than 7,500,000 centipoise, more preferably no more than 500,000 centipoise. Preferably the silicone elastomer blend has a viscosity of at least than 1,000 centipoise, more preferably at least 10,000 centipoise.

Other examples of silicones include silicone elastomers such as KSG6 (Shin-Etsu), Trefil E-505C or Trefil E-506C, now known as DC 9506 (dimethicone/vinyldimethicone crosspolymer, Dow-Corning and Toray), Gransil SR-CYC, SR DMF10, SR-DC556 (Grant Industries), KSP 100 and 200 series and KMP series (Shin Etsu), KSG15, KSG17, KSG16, and KSG18 (Shin-Etsu), Gransil SR 5CYC gel, Gransil SR DMF 10 gel, Gransil SR DC556 gel, SF 1204 and JK 113 (General Electric), DC 9040 (cyclomethicone and dimethicone crosspolymer blend, Dow Corning), DC 9701 (dimethicone/vinyl dimethicone cross-polymer coated with silica, Dow Corning). A mixture of these commercial products may also be used.

Solid Particles

Suitable solid particles include, but are not limited to ingredients which may be compounded in the composition of the present invention include inorganic powder such as gums, chalk, Fuller's earth, talc, kaolin, iron oxide, mica, sericite, muscovite, phlogopite, synthetic mica, lepidolite, biotite, lithia mica, vermiculite, magnesium carbonate, calcium carbonate, aluminum silicate, starch, smectite clays, alkyl and/or trialkyl aryl ammonium smectites, chemically modified magnesium aluminum silicate, organically modified montmorillonite clay, hydrated aluminum silicate, fumed silica, aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as ethylene acrylate, latex, polyamide resin powder (nylon powder), cyclodextrin, polyethylene powder, methyl polymethacrylate powder, polystyrene powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as titanium dioxide, zinc oxide, and magnesium oxide. Preferred organic powders/fillers include, but are not limited, to polymeric particles chosen from the methylsilsesquioxane resin microspheres such as for example those sold by Toshiba silicone under the name Tospearl 145A; microspheres of polymethylmethacrylates such as those sold by Seppic under the name Micropearl M 100; the spherical particles of crosslinked polydimethylsiloxanes, especially such as those sold by Dow Corning Toray Silicone under the name Trefil E 506C or Trefil E 505C, sphericle particles of polyamide and more specifically Nylon 12, especially such as those sold by Atochem under the name Orgasol 2002D Nat $CO_5$, polystyerene microspheres such as for example those sold by Dyno Particles under the name Dynospheres, ethylene acrylate copolymer sold by Kobo under the name FloBead EA209 and mixtures thereof.

Also useful herein are pigment and/or dye encapsulates such nanocolorants from BASF and multi-layer interference pigments such as Sicopearls from BASF.

Mixtures of the above powders may also be used.

Suitable solid particles are matting agents. The term "matting agent" means agents intended to make the skin visibly more matt and less shiny.

The matting effect of the agent and/or composition containing it may especially be evaluated using a gonioreflectometer, by measuring the ratio R from the specular reflection and the scattered reflection. A value of R of less than or equal to 2 generally reflects a matting effect.

The matting agent may especially be selected from among a rice starch or a corn starch, kaolinite, talc, a pumpkin seed extract, cellulose microbeads, plant fibers, synthetic fibers, in particular polyamide fibers, expanded acrylic copolymer microspheres, polyamide powders, silica powders, polytetrafluoroethylene powders, silicone resin powders, acrylic polymer powders, wax powders, polyethylene powders, powders of elastomeric crosslinked organopolysiloxane coated with silicone resin, talc/titanium dioxide/alumina/silica composite powders, amorphous mixed silicate powders, silicate particles and especially mixed silicate particles, and mixtures thereof.

Examples of matting agents that may especially be mentioned include:

rice or corn starch, in particular an aluminum starch octenyl succinate marketed under the trademark Dry Flo® by National Starch;

kaolinite;

silicas;

talc;

a pumpkin seed extract as marketed under the trademark Curbilene® by Indena;

cellulose microbeads;

fibers, such as silk fiber, cotton fiber, wool fiber, flax fiber, cellulose fiber extracted especially from wood, from vegetables or from algae, polyamide fiber (Nylon®), modified cellulose fiber, poly-p-phenyleneterephthamide fiber, acrylic fiber, polyolefin fiber, glass fiber, silica fiber, aramid fiber, carbon fiber, Teflon® fiber, insoluble collagen fiber, polyester fiber, polyvinyl chloride or polyvinylidene chloride fiber, polyvinyl alcohol fiber, polyacrylonitrile fiber, chitosan fiber, polyurethane fiber, polyethylene phthalate fiber, fibers formed from a mixture of polymers, resorbable synthetic fibers, expanded acrylic copolymer microspheres such as those marketed by EXPANCEL under the trademark Expancel 551®;

fillers with an optical effect, in particular:

polyamide powders (Nylon®), for instance Nylon 12 particles of the Orgasol type from Arkema, with a mean size of 10 microns and a refractive index of 1.54, silica powders, for instance Silica beads SB150 from Miyoshi with a mean size of 5 microns and a refractive index of 1.45, polytetrafluoroethylene powders, for instance PTFE Ceridust 9205F from Clariant, with a mean size of 8 microns and a refractive index of 1.36, silicone resin powders, for instance the silicone resin with trademarks Tospearl 150KA, Tospearl 1110A, Tospearl 120A, Tospearl 145A, Tospearl 2000B, Tospearl 3000A from Momentive, acrylic copolymer powders, especially of polymethyl(meth)acrylate, for instance the PMMA particles Jurymer MBI from Nihon Junyoki, or the Micropearl M100® and F 80 ED® particles from the company Matsumoto Yushi-Seiyaku, wax powders, for instance the paraffin wax particles Microease 114S from Micropowders, polyethylene powders, especially comprising at least one ethylene/acrylic acid copolymer, and in particular consisting of ethylene/acrylic acid copolymers, for instance the particles Flobeads EA 209 from Sumitomo, elastomeric crosslinked organopolysiloxane powders coated with silicone resin, especially with silsesquioxane resin. Such elastomeric powders are marketed under the trademarks KSP-100, KSP-101, KSP-102, KSP-103, KSP-104 and KSP-105 by Shin-Etsu, talc/titanium dioxide/alumina/silica composite powders such as those marketed under the trademark Coverleaf® AR-80 by Catalyst & Chemicals, and mixtures thereof, and compounds that absorb and/or adsorb sebum. And mention may be made especially of:

silica powders, for instance the porous silica microspheres marketed under the trademark Silica Beads SB-700 marketed by Miyoshi, the products Sunsphere® H51, Sunsphere® H33 and Sunsphere® H53 marketed by Asahi Glass; the polydimethylsiloxane-coated amorphous silica microspheres marketed under the trademark SA Sunsphere® H-33 and SA Sunsphere® H-53 marketed by Asahi Glass;

amorphous mixed silicate powders, especially of aluminum and magnesium, for instance the product marketed under the trademark Neusilin UFL2 by Sumitomo;

polyamide (Nylon®) powders, for instance Orgasol® 4000 marketed by Arkema, and acrylic polymer powders, especially of polymethyl methacrylate, for instance Covabead® LH85 marketed by Wacker; of polymethyl methacrylate/ethylene glycol dimethacrylate, for instance Dow Corning 5640 Microsponge® Skin Oil Adsorber marketed by Dow Corning, or Ganzpearl® GMP-0820 marketed by Ganz Chemical; of polyallyl methacrylate/ethylene glycol dimethacrylate, for instance Poly-Pore® L200 or Poly-Pore® E200 marketed by Amcol; of ethylene glycol dimethacrylate/lauryl methacrylate copolymer, for instance Polytrap® 6603 marketed by Dow Corning;

silicate particles, such as alumina silicate;

mixed silicate particles, such as:

magnesium aluminum silicate particles, such as saponite or hydrated magnesium aluminum silicate with a sodium sulfate marketed under the trademark Sumectone® by Kunimine;

the magnesium silicate, hydroxyethylcellulose, black cumin oil, marrow oil and phospholipids complex or Matipure® from Lucas Meyer, and mixtures thereof.

Other examples of matting agents are boron nitride particles, such as Softtouch CCS402, Softtouch CC6097, Softtouch CC6064.

Suitable solid particles are fillers with a Soft-Focus Effect. These fillers may be any material capable of modifying and hiding wrinkles by virtue of their intrinsic physical properties. These fillers may especially modify wrinkles via a tensioning effect, a covering effect or a soft-focus effect. Examples of such fillers include the following compounds:

porous silica microparticles, for instance the Silica Beads® SB150 and SB700 from Miyoshi with a mean size of 5 µm; the series-H Sunspheres® from Asahi Glass, hollow hemispherical silicone resin particles such as NLK 500®, NLK 506® and NLK 510® from Takemoto Oil and Fat;

silicone resin powders, for instance the silicone resin Tospearl® 145A from Momentive;

acrylic copolymer powders, especially of polymethyl (meth)acrylate, for instance the PMMA particles Jurymer MBI® from Nihon Junyoki, with a mean size of 8 µm, the hollow PMMA spheres marketed under the trademark Covabead® LH85 by Wacker, and vinylidene/acrylonitrile/methylene methacrylate expanded microspheres marketed under the trademark Expancel®;

wax powders, for instance the paraffin wax particles MicroEase® 114S from MicroPowders, with a mean size of 7 µm;

polyethylene powders, especially comprising at least one ethylene/acrylic acid copolymer, and in particular consisting of ethylene/acrylic acid copolymers, for instance the Flobeads® EA 209 particles from Sumitomo, with a mean size of 10 µm;

crosslinked elastomeric organopolysiloxane powders coated with silicone resin and especially with silsesquioxane resin, under the trademarks KSP-100®, KSP-101®, KSP-102®, KSP-103®, KSP-104® and KSP-105® by Shin-Etsu;

talc/titanium dioxide/alumina/silica composite powders, for instance those marketed under the trademark Coverleaf AR-80® by Catalyst & Chemicals;

talc, mica, kaolin, lauryl glycine, starch powders crosslinked with octenyl succinate anhydride, boron nitride, polytetrafluoroethylene powders, precipitated calcium carbonate, magnesium carbonate, magnesium hydrogen carbonate, barium sulfate, hydroxyapatite, calcium silicate, cerium dioxide and glass or ceramic microcapsules;

hydrophilic or hydrophobic, synthetic or unnatural, mineral or organic fillers such as silk fibers, cotton fibers, wool fibers, flax fibers, cellulose fibers extracted especially from wood, vegetables or algae, Polyamides (Nylon®) fibers, modified cellulose fibers, poly-p-terephthamide fibers, acrylic fibers, polyolefin fibers, glass fibers, silica fibers, aramid fibers, carbon fibers, polytetrafluoroethylene (Teflon®) fibers, insoluble collagen fibers, polyester fibers, polyvinyl chloride fibers, polyvinylidene chloride fibers, polyvinyl alcohol fibers, polyacrylonitriles fibers, chitosan fibers, polyurethane fibers, polyethylene phthalate fibers, fibers formed from a mixture of polymers, resorbable synthetic fibers, spherical elastomeric crosslinked silicones, for instance Trefil E-505C® or E-506C® from Dow Corning;

abrasive fillers, which, via a mechanical effect, smooth out the skin microrelief, such as abrasive silica, for instance Abrasif SP® from Semancz or nutshell powders (for example of apricot or walnut, from Cosmetochem).

The fillers with an effect on the signs of aging are especially selected from among porous silica microparticles, hollow hemispherical silicones, silicone resin powders, acrylic copolymer powders, polyethylene powders, crosslinked elastomeric organopolysiloxane powders coated with silicone resin, talc/titanium dioxide/alumina/silica composite powders, precipitated calcium carbonate, magnesium carbonate, magnesium hydrogen carbonate, barium sulfate, hydroxyapatite, calcium silicate, cerium dioxide, glass or ceramic microcapsules, and silk fibers or cotton fibers, and mixtures thereof.

The filler may be a soft-focus filler.

The term "soft-focus" filler means a filler which in addition gives the complexion transparency and a hazy effect. Preferably, the soft-focus fillers have a mean particle size of less than or equal to 15 microns. These particles may be in any form and in particular may be spherical or non-spherical. These fillers are more preferably non-spherical.

The soft-focus fillers may be selected from among silica and silicate powders, especially alumina powder, powders of polymethyl methacrylate (PMMA) type, talc, silica/$TiO_2$ or silica/zinc oxide composites, polyethylene powders, starch powders, polyamide powders, styrene/acrylic copolymer powders, silicone T-resin powders (for example with the tradename Tospearl from Momentive), silicone microspheres and silicone elastomers, and mixtures thereof.

Mention may be made in particular of talc with a number-average size of less than or equal to 3 microns, for example talc with a number-average size of 1.8 microns and especially the product marketed under the trademark Talc P3® by Nippon Talc, Nylon® 12 powder, especially the product marketed under the trademark Orgasol 2002 Extra D Nat Cos® by Atochem, silica particles 1% to 2% surface-treated with a mineral wax (INCI name: hydrated silica (and) paraffin) such as the products marketed by Degussa, amorphous silica microspheres, such as the products marketed under the trademark Sunsphere, for example of reference H-53® by Asahi Glass, and silica microbeads such as those marketed under the trademark SB-700® or SB-150® by Miyoshi, this list not being limiting.

Inorganic Sunscreens

The additional mineral screening agents are selected from among coated or uncoated metal oxide pigments in which the mean size of the primary particles is preferentially from 5 nm to 100 nm (preferably from 10 nm to 50 nm), for instance titanium oxide (amorphous or crystallized in rutile and/or anatase form), iron oxide, zinc oxide, zirconium oxide or cerium oxide pigments, which are all UV-photo-protective agents that are well known per se.

The pigments may be coated or uncoated.

The coated pigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminum salts of fatty acids, metal alkoxides (of titanium or of aluminum), polyethylene, silicones, proteins (collagen, elastin), alkanolamines, silicon oxides, metal oxides or sodium hexametaphosphate.

As is known, silicones are organosilicon polymers or oligomers of linear or cyclic, branched or crosslinked structure, of variable molecular weight, obtained by polymerization and/or polycondensation of suitably functionalized silanes, and consist essentially of a repetition of main units in which the silicon atoms are linked together via oxygen atoms (siloxane bond), optionally substituted hydrocarbon-based radicals being directly attached via a carbon atom to the said silicon atoms.

The term "silicones" also includes the silanes required for their preparation, in particular alkyl silanes.

The silicones used for coating the nanopigments that are suitable for the present invention are preferably selected from among the group containing alkyl silanes, polydialkylsiloxanes and polyalkylhydrogenosiloxanes. Even more preferentially, the silicones are selected from among the group containing octyltrimethylsilane, polydimethylsiloxanes and polymethylhydrogenosiloxanes.

Before being treated with silicones, the metal oxide pigments may have been treated with other surface agents, in particular with cerium oxide, alumina, silica, aluminum compounds or silicon compounds, or mixtures thereof.

The coated pigments are more particularly titanium oxides that have been coated: with silica, such as the product Sunveil from the company Ikeda and the product Eusolex T-AVO from the company Merck, with silica and iron oxide, such as the product Sunveil F from the company Ikeda, with silica and alumina, such as the products Microtitanium Dioxide MT 500 SA and Microtitanium Dioxide MT 100

SA from the company Tayca, Tioveil from the company Tioxide and Mirasun TiW 60 from the company Rhodia,
with alumina, such as the products Tipaque TTO-55 (B) and Tipaque TTO-55 (A) from the company Ishihara and UVT 14/4 from the company Kemira,
with alumina and aluminum stearate, such as the product Microtitanium Dioxide MT 100 TV, MT 100 TX, MT 100 Z and MT-01 from the company Tayca, and the products Solaveil CT-10 W, Solaveil CT 100 and Solaveil CT 200 from the company Uniqema,
with silica, alumina and alginic acid, such as the product MT-100 AQ from the company Tayca,
with alumina and aluminum laurate, such as the product Microtitanium Dioxide MT 100 S from the company Tayca,
with iron oxide and iron stearate, such as the product Microtitanium Dioxide MT 100 F from the company Tayca,
with zinc oxide and zinc stearate, such as the product BR351 from the company Tayca,
with silica and alumina and treated with a silicone, such as the products Microtitanium Dioxide MT 600 SAS, Microtitanium Dioxide MT 500 SAS or Microtitanium Dioxide MT 100 SAS from the company Tayca,
with silica, alumina and aluminum stearate and treated with a silicone, such as the product STT-30-DS from the company Titan Kogyo,
with silica and treated with a silicone, such as the product UV-Titan X 195 from the company Kemira, or the product SMT-100 WRS from the company Tayca,
with alumina and treated with a silicone, such as the products Tipaque TTO-55 (S) from the company Ishihara or UV Titan M 262 from the company Kemira,
with triethanolamine, such as the product STT-65-S from the company Titan Kogyo,
with stearic acid, such as the product Tipaque TTO-55 (C) from the company Ishihara,
with sodium hexametaphosphate, such as the product Microtitanium Dioxide MT 150 W from the company Tayca.

Other titanium oxide pigments treated with a silicone are preferably $TiO_2$ treated with octyltrimethylsilane and for which the mean size of the elementary particles ranges from 25 to 40 nm, such as the product marketed under the trademark T 805 by Degussa Silices, $TiO_2$ treated with a polydimethylsiloxane and for which the mean size of the elementary particles is 21 nm, such as the product marketed under the trademark 70250 Cardre UF TiO2SI3 by Cardre, anatase/rutile $TiO_2$ treated with a polydimethylhydrogenosiloxane and for which the mean size of the elementary particles is 25 nm, such as the product marketed under the trademark Microtitanium Dioxide USP Grade Hydrophobic by Color Techniques.

The uncoated titanium oxide pigments are marketed, for example, by Tayca under the trademarks Microtitanium Dioxide MT 500 B or Microtitanium Dioxide MT 600 B, by Degussa under the trademark P 25, by Wacker under the trademark Transparent titanium oxide PW, by Miyoshi Kasei under the trademark UFTR, by Tomen under the trademark ITS and by Tioxide under the trademark Tioveil AQ.

The uncoated zinc oxide pigments are, for example:
those marketed under the trademark Z-Cote by Sunsmart;
those marketed under the trademark Nanox by Elementis;
those marketed under the trademark Nanogard WCD 2025 by Nanophase Technologies.

The coated zinc oxide pigments are, for example:
those marketed under the trademark Z-Cote HP1 by Sunsmart (dimethicone-coated ZnO);
those marketed under the trademark Zinc Oxide CS-5 by Toshibi (ZnO coated with polymethylhydrogenosiloxane);
those marketed under the trademark Nanogard Zinc Oxide FN by Nanophase Technologies (as a 40% dispersion in Finsolv TN, $C_{12}$-$C_{15}$ alkyl benzoate);
those marketed under the trademark Daitopersion ZN-30 and Daitopersion ZN-50 by Daito (dispersions in cyclopolymethylsiloxane/oxyethylenated polydimethylsiloxane, containing 30% or 50% of nanozinc oxides coated with silica and polymethylhydrogenosiloxane);
those marketed under the trademark NFD Ultrafine ZnO by Daikin (ZnO coated with perfluoroalkyl phosphate and copolymer based on perfluoroalkylethyl as a dispersion in cyclopentasiloxane);
those marketed under the trademark SPD-Z1 by Shin-Etsu (ZnO coated with silicone-grafted acrylic polymer, dispersed in cyclodimethylsiloxane);
those marketed under the trademark Escalol Z100 by ISP (alumina-treated ZnO dispersed in an ethylhexyl methoxycinnamate/PVP-hexadecene/methicone copolymer mixture);
those marketed under the trademark Fuji ZnO-SMS-10 by Fuji Pigment (ZnO coated with silica and polymethylsilsesquioxane);
those marketed under the trademark Nanox Gel TN by Elementis (ZnO dispersed at a concentration of 55% in $C_{12}$-$C_{15}$ alkyl benzoate with hydroxystearic acid polycondensate).

The uncoated cerium oxide pigments are marketed under the trademark Colloidal Cerium Oxide by Rhone-Poulenc.

The uncoated iron oxide nanopigments are marketed, for example, by Arnaud under the trademarks Nanogard WCD 2002 (FE 45B), Nanogard Iron FE 45 BL AQ, Nanogard FE 45R AQ and Nanogard WCD 2006 (FE 45R) or by Mitsubishi under the trademark TY-220.

The coated iron oxide pigments are marketed, for example, by Arnaud under the trademarks Nanogard WCD 2008 (FE 45B FN), Nanogard WCD 2009 (FE 4513 556), Nanogard FE 45 BL 345 and Nanogard FE 45 BL or by BASF under the trademark Transparent Iron Oxide.

Also exemplary are mixtures of metal oxides, especially of titanium dioxide and of cerium dioxide, including the silica-coated equal-weight mixture of titanium dioxide and of cerium dioxide, marketed by Ikeda under the trademark Sunveil A, and also the alumina, silica and silicone-coated mixture of titanium dioxide and of zinc dioxide, such as the product M 261 marketed by Kemira, or the alumina, silica and glycerol-coated mixture of titanium dioxide and of zinc dioxide, such as the product M 211 marketed by Kemira.

The additional UV-screening agents are generally present in the compositions according to the invention in proportions ranging from 0.01% to 20% by weight relative to the total weight of the composition, and preferably ranging from 0.1% to 10% by weight relative to the total weight of the composition.

Organic Solvents

Among the organic solvents that are exemplary are lower alcohols and polyols. These polyols may be selected from among glycols and glycol ethers, for instance ethylene glycol, propylene glycol, butylene glycol, dipropylene glycol or diethylene glycol.

Thickeners

Hydrophilic thickeners that are exemplary include carboxyvinyl polymers such as the Carbopol products (carbomers) and the Pemulen products (acrylate/$C_{10}$-$C_{30}$-alkylacrylate copolymer); polyacrylamides, for instance the crosslinked copolymers marketed under the trademarks Sepigel 305 (CTFA name: polyacrylamide/$C_{13-14}$ isoparaffin/Laureth 7) or Simulgel 600 (CTFA name: acrylamide/sodium acryloyldimethyltaurate copolymer/isohexadecane/polysorbate 80) by SEPPIC; 2-acrylamido-2-methylpropanesulfonic acid polymers and copolymers, which are optionally crosslinked and/or neutralized, for instance the poly(2-acrylamido-2-methylpropanesulfonic acid) marketed by Hoechst under the trademark Hostacerin AMPS (CTFA name: ammonium polyacryloyldimethyltaurate) or Simulgel 800 marketed by SEPPIC (CTFA name: sodium polyacryloyldimethyltaurate/polysorbate 80/sorbitan oleate); copolymers of 2-acrylamido-2-methylpropanesulfonic acid and of hydroxyethyl acrylate, for instance Simulgel NS and Sepinov EMT 10 marketed by SEPPIC; cellulose-based derivatives such as hydroxyethylcellulose; polysaccharides and especially gums such as xanthan gum; and mixtures thereof; starch and starch derivatives, associative thickeners, polyurethane based thickeners.

Lipophilic thickeners that are exemplary include synthetic polymers such as poly($C_{10}$-$C_{30}$ alkyl acrylates) marketed under the trademark Intelimer IPA 13-1 and Intelimer IPA 13-6 by Landec, or modified clays such as hectorite and its derivatives, for instance the products marketed under the trademark Bentone.

The compositions according to the invention may be formulated according to techniques that are well known to one skilled in this art. They may be in particular in the form of a simple or complex emulsion (O/W, W/O, O/W/O or W/O/W emulsion) such as a cream, a milk or a cream-gel; in the form of an aqueous gel; in the form of a lotion. They may optionally be packaged as an aerosol and may be in the form of a mouse or a spray.

The compositions according to the invention are preferably in the form of an oil-in-water or water-in-oil emulsion.

Emulsifiers

The emulsions can contain emulsifiers selected from among amphoteric, anionic, cationic and nonionic emulsifiers, which are used alone or as a mixture. The emulsifiers are appropriately selected according to the emulsion to be obtained (W/O or O/W). The emulsions may also contain stabilizers of other types, for instance fillers, gelling polymers or thickeners.

As emulsifying surfactants that may be used for the preparation of the W/O emulsions, examples include sorbitan, glycerol or sugar alkyl esters or ethers; silicone surfactants, for instance dimethicone copolyols, such as the mixture of cyclomethicone and of dimethicone copolyol, marketed under the trademark DC 5225 C by Dow Corning, and alkyldimethicone copolyols such as laurylmethicone copolyol marketed under the trademark Dow Corning 5200 Formulation Aid by Dow Corning; cetyldimethicone copolyol, such as the product marketed under the trademark Abil EM 90R by Goldschmidt, and the mixture of cetyldimethicone copolyol, of polyglyceryl isostearate (4 mol) and of hexyl laurate, marketed under the trademark Abil WE 09 by Goldschmidt. Other examples are the silicone emulsifiers from Momentive under the trademarks SF1528, SF1540, Silform EOF, Silform 60-A.

One or more co-emulsifiers may also be added thereto, which may be selected advantageously from the group comprising polyol alkyl esters.

Polyol alkyl esters that are especially exemplary include polyethylene glycol esters, for instance PEG-30 dipolyhydroxystearate, such as the product marketed under the trademark Arlacel P135 by ICI.

Glycerol and/or sorbitan esters that are especially exemplary include, for example, polyglyceryl isostearate, such as the product marketed under the trademark Isolan GI 34 by Goldschmidt, sorbitan isostearate, such as the product marketed under the trademark Arlacel 987 by ICI, sorbitan glyceryl isostearate, such as the product marketed under the trademark Arlacel 986 by ICI, and mixtures thereof.

For the O/W emulsions, examples of emulsifiers include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters, for instance the mixture PEG-100 stearate/glyceryl stearate marketed, for example, by ICI under the trademark Arlacel 165; oxyalkylenated (oxyethylenated and/or oxypropylenated) fatty alkyl ethers; sugar esters, for instance sucrose stearate; fatty alkyl ethers of sugars, especially polyalkylglucosides (APG) such as decylglucoside and laurylglucoside marketed, for example, by Henkel under the respective names Plantaren 2000 and Plantaren 1200, cetostearyl glucoside optionally as a mixture with cetostearyl alcohol, marketed, for example, under the trademark Montanov 68 by SEPPIC, under the trademark Tegocare CG90 by Goldschmidt and under the trademark Emulgade KE3302 by Henkel, and also arachidyl glucoside, for example in the form of a mixture of arachidyl alcohol, behenyl alcohol and arachidyl glucoside, marketed under the trademark Montanov 202 by SEPPIC. Examples of silicones emulsifiers, suitable for O/W emulsions are the polyether siloxane copolymers under the trademarks, SF1188A, SF1288, Silsoft 880, Silsoft 860, Silsoft 440, Silsoft 895, Silsoft 900.

Among the other emulsion stabilizers that will be used more particularly are isophthalic acid or sulfoisophthalic acid polymers, and in particular phthalate/sulfoisophthalate/glycol copolymers, for example the diethylene glycol/phthalate/isophthalate/1,4-cyclohexanedimethanol copolymer (INCI name: Polyester-5) marketed under the trademark Eastman AQ Polymer (AQ35S, AQ38S, AQ55S and AQ48 Ultra) by Eastman Chemical.

Other suitable emulsifiers are the amino-based emulsifiers, such as sodium stearoyl glutamate and phospholipids such as lecithin, hydroxylated lecithin Film-Forming Polymer According to preferred embodiments of the present invention, the compositions may comprise at least one additional film-forming polymer.

In the present invention, the term "film-forming polymer" means a polymer that is capable, by itself or in the presence of an auxiliary film-forming agent, of forming a macroscopically continuous deposit on keratin materials. The composition may comprise an aqueous phase, and the film-forming polymer may be present in this aqueous phase. In this case, it will preferably be a polymer in dispersion or an amphiphilic or associative polymer.

The term polymer in dispersion" means water-insoluble polymers present in the form of particles of variable size. The polymer may or may not be crosslinked. The size of the polymer particles is typically between 25 and 500 nanometers and preferably between 50 and 200 nanometers. The following polymers in aqueous dispersion may be used: Ultrasol 2075 from Ganz Chemical, Daitosol 5000 AD from Daito Kasei, Avalure UR 450 from Noveon, DynamX from National Starch, Syntran 5760 from Interpolymer, Acusol OP 301 from Roehm & Haas, and Neocryl A 1090 from Avecia.

The acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® or Daitosol 5000 SJ® by the company Daito Kasey Kogyo; Syntran 5760® by the company Interpolymer, Soltex OPT by the company Roehm & Haas, aqueous dispersions of acrylic or styrene/acrylic polymers sold under the brand name Joncryl® by the company Johnson polymer, or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer; the sulfopolyesters sold under the brand name Eastman AQ® by the company Eastman Chemical Products, and vinyl dispersions, for instance Mexomer PAM® from the company Chimex, and mixtures thereof, are other examples of aqueous dispersions of water-dispersible film-forming polymer particles.

The term "amphiphilic or associative polymers" means polymers comprising one or more hydrophilic parts that make them partially water-soluble and one or more hydrophobic parts via which the polymers associate or interact. The following associative polymers may be used: Nuvis FX 1100 from Elementis, Aculyn 22, Aculyn 44 and Aculyn 46 from Roehm & Haas, Viscophobe DB 1000 from Amerchol. Diblock copolymers formed from a hydrophilic block (polyacrylate or polyethylene glycol) and from a hydrophobic block (polystyrene or polysiloxane) may also be used.

The composition may comprise an oily phase and the film-forming polymer may be present in this oily phase. The polymer may then be in dispersion or in solution.

As examples of lipodispersible non-aqueous film-forming polymer dispersions in the form of non-aqueous dispersions of polymer particles in one or more silicone and/or hydrocarbon-based oils, which may be surface-stabilized with at least one stabilizer, especially a block, grafted or random polymer, mention may be made of acrylic dispersions in isododecane, for instance Mexomer PAP® from the company Chimex, and dispersions of particles of a grafted ethylenic polymer, preferably an acrylic polymer, in a liquid fatty phase, the ethylenic polymer advantageously being dispersed in the absence of additional stabilizer at the surface of the particles as described especially in document WO 04/055 081.

Among the film-forming polymers that may be used in the composition of the present invention, mention may be made of synthetic polymers, of free-radical type or of polycondensate type, and polymers of natural origin, and mixtures thereof.

The expression "free-radical film-forming polymer" means a polymer obtained by polymerization of unsaturated and especially ethylenically unsaturated monomers, each monomer being capable of homopolymerizing (unlike polycondensates).

The film-forming polymers of free-radical type may especially be vinyl polymers or copolymers, especially acrylic polymers.

The vinyl film-forming polymers may result from the polymerization of ethylenically unsaturated monomers containing at least one acidic group and/or esters of these acidic monomers and/or amides of these acidic monomers.

Monomers bearing an acidic group that may be used are $\alpha,\beta$-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid.

The esters of acidic monomers are advantageously chosen from (meth)acrylic acid esters (also known as (meth)acrylates), especially (meth)acrylates of an alkyl, in particular of a $C_1$-$C_{30}$ and preferably $C_1$-$C_{20}$ alkyl, (meth)acrylates of an aryl, in particular of a $C_6$-$C_{10}$ aryl, and (meth)acrylates of a hydroxyalkyl, in particular of a $C_2$-$C_6$ hydroxyalkyl.

The film-forming polymer may be chosen from block or random polymers and/or copolymers especially comprising polyurethanes, polyacrylics, silicones, fluoro polymers, butyl rubbers, ethylene copolymers, natural gums and polyvinyl alcohols, and mixtures thereof.

The vinyl film-forming polymers may also result from the homopolymerization or copolymerization of monomers chosen from vinyl esters and styrene monomers.

Examples of vinyl esters that may be mentioned are vinyl acetate, vinyl neodecanoate, vinyl pivalate, vinyl benzoate and vinyl t-butylbenzoate.

Styrene monomers that may be mentioned are styrene and $\alpha$-methylstyrene.

Among the film-forming polycondensates that may be mentioned are polyurethanes, polyesteramides, polyamides, epoxyester resins, polyureas and polyesters.

The polyurethanes may be chosen from anionic, cationic, nonionic and amphoteric polyurethanes, polyurethane-acrylics, polyurethane-polyvinylpyrrolidones, polyester-polyurethanes, polyether-polyurethanes, polyureas and polyurea-polyurethanes, and mixtures thereof.

Examples of liposoluble polymers that may be mentioned are copolymers of vinyl ester (the vinyl group being directly linked to the oxygen atom of the ester group and the vinyl ester containing a saturated, linear or branched hydrocarbon-based radical of 1 to 19 carbon atoms, linked to the carbonyl of the ester group) and of at least one other monomer which may be a vinyl ester (other than the vinyl ester already present), an $\alpha$-olefin (containing from 8 to 28 carbon atoms), an alkyl vinyl ether (in which the alkyl group comprises from 2 to 18 carbon atoms) or an allylic or methallylic ester (containing a saturated, linear or branched hydrocarbon-based radical of 1 to 19 carbon atoms, linked to the carbonyl of the ester group).

These copolymers may be crosslinked with the aid of crosslinking agents, which may be either of the vinyl type or of the allylic or methallylic type, such as tetraallyloxyethane, divinylbenzene, divinyl octanedioate, divinyl dodecanedioate and divinyl octadecanedioate. Examples of liposoluble film-forming polymers that may be mentioned include copolymers of a vinyl ester and of at least one other monomer that may be a vinyl ester, especially vinyl neodecanoate, vinyl benzoate and vinyl t-butylbenzoate, an $\alpha$-olefin, an alkyl vinyl ether or an allylic or methallylic ester.

Examples of liposoluble film-forming polymers that may also be mentioned are liposoluble copolymers, and in particular those resulting from the copolymerization of vinyl esters containing from 9 to 22 carbon atoms or of alkyl acrylates or methacrylates, and alkyl radicals containing from 10 to 20 carbon atoms.

Such liposoluble copolymers may be chosen from copolymers of polyvinyl stearate, polyvinyl stearate crosslinked with the aid of divinylbenzene, of diallyl ether or of diallyl phthalate, polystearyl (meth)acrylate, polyvinyl laurate and polylauryl (meth)acrylate, it being possible for these poly (meth)acrylates to be crosslinked with the aid of ethylene glycol dimethacrylate or tetraethylene glycol dimethacrylate.

The liposoluble copolymers defined above are known and are described in particular in patent application FR-A-2 232 303; they may have a weight-average molecular weight ranging from 2000 to 500 000 and preferably from 4000 to 200 000.

As liposoluble film-forming polymers that may be used in the invention, mention may also be made of polyalkylenes and in particular copolymers of C2-C20 alkenes, such as polybutene, alkylcelluloses with a linear or branched, saturated or unsaturated C1-C8 alkyl radical, for instance ethylcellulose and propylcellulose.

A preferred at least one film forming polymer for use in the compositions of the present invention is chosen from copolymers of vinyl acetate and copolymers of vinylpyrrolidone such as allyl stearate/vinyl acetate copolymer, commercially available from Chimex under the trade name Mexomere PQ®, VP/hexadecene copolymer, commercially available from International Specialty Products (ISP) under the trade names Antaron® V 216 or Ganex® V 216, and VP/eicosene copolymer, commercially available from ISP under the trade names Antaron® V 220 or Ganex® V 220.

The at least one film-forming polymer may be present in the composition of the present invention in an amount ranging from about 0.1% to about 30% by weight; such as from about 0.5% to about 20% by weight; such as from about 1% to about 10% by weight based on the total weight of the composition, including all ranges and subranges therebetween.

Styling Polymers

The styling polymers may be chosen from nonionic, anionic, cationic, and amphoteric polymers and mixtures thereof. The styling polymer may additionally be halogenated, in particular fluorinated.

The styling polymers can be used in solubilized form or else in the form of dispersions of solid polymer particles (latex or pseudo-latex).

The nonionic styling polymers useful according to the present invention are polyurethanes and N-vinylpyrrolidone polymers and copolymers. Nonionic polymers containing N-vinylpyrrolidone in various weight average molecular weights are available commercially from ISP Corporation—specific examples of such materials are homopolymers of N-vinylpyrrolidone having an average molecular weight of about 630,000 sold under the name PVP K-90 and are homopolymers of N-vinylpyrrolidone having an average molecular weight of about 1,000,000 sold under the name of PVP K-120.

Particularly preferred styling polymers are polyvinylpyrrolidone, vinylpyrrolidone/vinyl acetate copolymer, AMP-acrylates/allyl methacrylate copolymer (commercially available from Noveon under the tradename, Fixate G-100), sodium polystyrene sulfonate (commercially available from National Starch under the tradename, Flexan II), Vinylpyrrolidone/acrylates/lauryl methacyrlate copolymer (commercially available from ISP under the tradename, Acrylidone LM), polyquaternium-6, and polyurethane-2 (commercially available from Noveon under the tradename, Avalure 405 or 410) or polyurethane polymers, commercially available from Bayer under the trademark Baycusan.

Preservatives

Suitable traditional preservatives for compositions of this invention are alkyl esters of para-hydroxybenzoic acid. Other preservatives which have more recently come into use include hydantoin derivatives such as 1,3-bis(hydroxymethyl)-5,5-dimthylhydantoin, propionate salts, and a variety of quaternary ammonium compounds such as benzalkonium chloride, quaternium 15 (Dowicil 200), benzethonium Chloride, and methylbenzethonium chloride. Suitable preservatives are also organic acids such as sorbic acid, potassium sorbate, levulinic acid, anisic acid. Other types of preservatives are isothiazolinones (Kathon), formaldehyde releasers (diazolidinyl urea, imidazolidinyl urea), parabens (methyl paraben, propyl paraben). Other suitable preservatives are Cosmetic chemists are familiar with appropriate preservatives and routinely choose them to satisfy the preservative challenge test and to provide product stability. Suitable preservatives are benzyl alcohol, mixture of ethylhexylglycerin with benzyl alcohol, 2-bromo-2 nitropropane 1,3 diol, disodium EDTA, phenoxyethanol, mixture of phenoxyethanol and ethylhexylglycerin, phenethyl alcohol, sodium dehydroacetate and benzyl alcohol. Preservatives can be blended with preservative boosters for example caprylyl glycol, sorbitan caprylate, ethylhexylglycerin. The preservatives should be selected having regard for the use of the composition and possible incompatibilities between the preservatives and other ingredients in the emulsion. Preservatives preferably are employed in amounts ranging from about 0% to about 5%, more preferably from about 0.01% to about 2.5%, and most preferably from about 0.01% to about 1%, by weight of the composition.

Additional Actives

The additional active agents may be selected especially from among moisturizers, desquamating agents, agents for improving the skin barrier function, depigmenting agents, antioxidants, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, agents for promoting the maturation of the horny envelope, NO-synthase inhibitors, peripheral benzodiazepine receptor (PBR) antagonists, agents for increasing the activity of the sebaceous glands, agents for stimulating the energy metabolism of cells, tensioning agents, lipo-restructuring agents, slimming agents, agents for promoting the cutaneous capillary circulation, calmatives and/or anti-irritants, sebo-regulators or anti-seborrhoeic agents, astringents, cicatrizing agents, anti-inflammatory agents and anti-acne agents.

One skilled in this art will select the said active agent(s) as a function of the effect desired on the skin, the hair, the eyelashes, the eyebrows and the nails.

The composition may also comprise at least one ingredient such as fillers with a soft-focus effect or agents for promoting the natural coloration of the skin, useful for complementing the biological effects of these active agents or for providing an immediate visual anti-aging effect.

For caring for and/or making up greasy skin, one skilled in this art will preferably select at least one active agent selected from among desquamating agents, sebo-regulating agents or anti-seborrhoeic agents, and astringents.

The composition may also comprise at least one additional ingredient for complementing the biological effect of these active agents or for providing an immediate visual effect; especially exemplary are matting agents, fillers with a soft-focus effect, fluorescers, agents for promoting the naturally pinkish coloration of the skin, and abrasive fillers or exfoliants.

The composition of the present invention has low viscosity and can be used to formulate a wide variety of ingredients, such as fatty substances, humectants, solid particles, silicones, organic or inorganic sunscreens, without the need of dispersants or emulsifiers.

In one embodiment there is provided a personal care composition, a cosmetic composition, a textile composition, an oil extraction composition, a coating composition, a paint composition, an agrochemical composition, a lubrication composition, a composition requiring irreversible thickening, and an emulsification composition comprising a composition made by the process described herein.

In one further embodiment there is provided a hair care or skin care application comprising a composition made by the process described herein.

EXAMPLES

Example 1

Preparation of the Aminosilicone Copolymer A

A 1000 ml four-necked flask fitted with a mechanical stirrer, a condenser fitted with a nitrogen outlet and a thermometer was charged with 80.0 g of amino-functionalized polymer Jeffamine M-2005 and 212.4 g of isopropanol. The mixture was heated with stirring to 80° C. The epoxy-terminated polysiloxane $[CH_2(O)CHCH_2O(CH_2)_3Si(CH_3)_2[OSi(CH_3))_2]_{100}OSi(Me_2)(CH_2)_3OCH_2CH(O)CH_2]$ were added to the flask at 80° C. The reaction was run at 80° C. with stirring. The reaction was completed when the epoxy functionality, determined by titration, was consumed. This typically required 6 to 10 hours. The isopropanol solvent was stripped by vacuum nitrogen sparge.

Preparation of the Intermediate Wax Composition

The intermediate wax composition was made in a Ross double planetary mixer (DPM 1QT). The aminosilicone copolymer A (350 g) and the ester isopropylmyristate (IPM) (350 g) were charged and mixed at room temperature for 1 hour. The hydrophilic polymer Carbopol 1382 powder (polyacrylic crosspolymer) (87.5 g) was charged. The mixture of hydrophobic polymer, the hydrophilic polymer carbopol 1382 and the isopropylmyristate was stirred for 40 min at 30 C. Dionized water (7.9 g) was added and the mixture was mixed at 30° C. for 30 min. The mixture was heated to 90° C. and stirred for 6 hour at low speed (30 rpm). During the heating, the mixture thickened and became a thick viscous paste. After 6 hours at high temperature, the mixture was cooled to room temperature.

Preparation of the Composition of the Present Invention

The next day, the intermediate wax composition was heated to 55° C. The 20% aqueous solution of amino methyl propanol (AMP), 261.9 g was added to the warm intermediate wax composition while stirring at medium speed.

After all the AMP solution addition was completed, the blend was stirred at 55° C. for 2 hour. The neutralized blend was cooled at room temperature and discharged.

Finally, the batch was homogenized in an Omni homogenizer with a saw-tooth rotor 35 mm diameter at 7000 rpm for 5 min. The final pH was around 7. The composition had a viscosity of 24800 cp. When diluted with water at 3 wt %, it produced a thickened emulsion with a viscosity of 19600 cp.

Comparative Example 1

The intermediate wax composition was made in a Ross double planetary mixer (DPM 1QT). The aminosilicone copolymer A of example 1 (82.93 g) and the ester isopropylmyristate (IPM) (82.93 g) were charged and mixed at room temperature for 1 hour. The hydrophilic polymer Carbopol 1382 powder (polyacrylic crosspolymer) (20.73 g) was charged. The mixture of the aminosilicone copolymer, the hydrophilic polymer carbopol 1382 and the isopropylmyristate was stirred for 40 min at 30° C. The mixture was heated to 120° C. and stirred for 2.67 hour at low speed (30 rpm). During the heating, the mixture thickened and became a thick viscous paste. After 2.67 hours at high temperature, the mixture was cooled to room temperature.

The next day, the intermediate wax composition was heated to 55° C. The 20% aqueous solution of amino methyl propanol (AMP), 63.43 g was added to the warm intermediate wax composition while stirring at medium speed.

After all the AMP solution addition was completed, the blend was stirred at 55° C. for 2 hour. The neutralized blend was cooled at room temperature and discharged.

Finally, the batch was homogenized in an Omni homogenizer with a saw-tooth rotor 35 mm diameter at 7000 rpm for 5 min. The final pH was around 7. The composition had a viscosity of 80600 cp. When diluted with water at 3 wt %, it produced an emulsion with a viscosity of less than 1000 cp.

Example 2

The aminosilicone copolymer used in this example is prepared using the method described above.

Preparation of the Intermediate Wax Composition

The intermediate wax composition was made in a Ross double planetary mixer (DPM 1QT). The aminosilicone copolymer (350 g) and the ester isopropylmyristate (IPM) (350 g) were charged and mixed at room temperature for 1 hour. The hydrophilic polymer Carbopol 1382 powder (polyacrylic crosspolymer) (87.5 g) was charged. The mixture of hydrophobic polymer, the hydrophilic polymer carbopol 1382 and the isopropylmyristate was stirred for 40 min at 30 C. Dionized water (7.9 g) was added and the mixture was mixed at 30° C. for 30 min. The mixture was heated to 90° C. and stirred for 6 hour at low speed (30 rpm). During the heating, the mixture thickened and became a thick viscous paste. After 6 hours at high temperature, the mixture was cooled to room temperature.

Preparation of the Composition of the Present Invention

The next day, the intermediate wax composition was heated to 55° C. The 30% aqueous solution of Trisamino, 267.7 g was added to the warm intermediate wax composition while stirring at medium speed.

After all the Trisamino solution addition was completed, the blend was stirred at 55° C. for 2 hour. The neutralized blend was cooled at room temperature and discharged.

Finally, the batch was homogenized in an Omni homogenizer with a saw-tooth rotor 35 mm diameter at 7000 rpm for 5 min. The final pH was around 7. The composition had a viscosity of 15900 cp. When diluted with water at 3 wt %, it produced a thickened emulsion with a viscosity of 18400 cp.

Comparative Example 2

The aminosilicone copolymer (hydrophobic polymer) used in this example is prepared like the one of example 1.

Preparation of the Intermediate Wax Composition

The intermediate wax composition was made in a Ross double planetary mixer (DPM 1QT). The aminosilicone copolymer (99.51 g) and the ester isopropylmyristate (IPM) (99.51 g) were charged and mixed at room temperature for 1 hour. The hydrophilic polymer Carbopol 1382 powder (polyacrylic crosspolymer) (24.87) was charged. The mixture of aminosilicone copolymer, the hydrophilic polymer carbopol 1382 and the isopropylmyristate was stirred for 40 min at 30° C. The mixture was heated to 120° C. and stirred for 2.67 hours at low speed (30 rpm). During the heating, the mixture thickened and became a thick viscous paste. After 2.67 hours at high temperature, the mixture was cooled to room temperature.

Preparation of the Composition of the Present Invention

The next day, the intermediate wax composition was heated to 55° C. The 30% aqueous solution of Trisamino, 76.11 g was added to the warm intermediate wax composition while stirring at medium speed.

After all the Trisamino solution addition was completed, the blend was stirred at 55° C. for 2 hour. The neutralized blend was cooled at room temperature and discharged.

Finally, the batch was homogenized in an Omni homogenizer with a saw-tooth rotor 35 mm diameter at 7000 rpm for 5 min. The final pH was around 7. The composition had a viscosity of 96000cp. When diluted with water at 3 wt %, it produced an emulsion with a viscosity of less than 1000 cp.

Example 3 and Example 4 are made similarly to Example 1 and 2 respectively. Comparative example 3 and Comparative example 4 are made similarly to Comparative example 1 and Comparative example 2 respectively. Table 1 shows a summary of the examples 1-4 and comparative examples 1-4.

TABLE 1

Compositions according to the invention and comparatives

| Components | Ex. 1 | Ex. 2 | Ex. 3 | Ex. 4 | Comp. 1 | Comp. 2 | Comp. 3 | Comp. 4 |
| --- | --- | --- | --- | --- | --- | --- | --- | --- |
| Aminosilicone copolymer | 350 | 350 | 962 | 345.6 | 82.93 | 99.51 | 99.51 | 99.51 |
| Isopropylmyristate | 350 | 350 | 962 | 345.6 | 82.93 | 99.51 | 99.51 | 99.51 |
| Carbopol 1382 | 87.5 | 87.5 | 240.4 | 86.4 | 20.73 | 24.87 | 24.87 | 24.87 |
| Water (added in step (i)) | 7.9 | 7.9 | 21.7 | 7.8 | 0 | 0 | 0 | 0 |
| 20% solution of amino methyl propanol | 261.9 | | 743.1 | | 63.43 | | 76.11 | |
| 30% solution of trisamino | | 267.7 | | 264.3 | | 76.11 | | 76.11 |
| Temperature in step (i) (° C.) | 90 | 90 | 90 | 90 | 120 | 120 | 120 | 120 |
| Reaction time in step (i) (h) | 6 | 6 | 6 | 6 | 2.67 | 2.67 | 3.5 | 3.5 |
| pH | 7 | 7 | 7 | 7 | 7 | 7 | 7 | 7 |
| Viscosity @ 25° C. (cps) | 24800 | 15900 | 40200 | 20100 | 80600 | 96000 | 147800 | 309000 |
| Viscosity after dilution in water (3% wt in water) (cps) | 19600 | 18400 | 23500 | 30600 | <1000 | <1000 | <1000 | <1000 |

The examples which contained water in step 1 produced gels which were easy to use because they were not too viscous (viscosity<50000 cp) and they produced thick emulsion when diluted with water with viscosity higher than 15000 cp at 3% wt.

Example 5

The composition prepared according to the present invention was combined with the water phase and stirred with a U-shape blade with a conventional overhead mixer for 1 hour to form an aqueous gel. The organic sunscreens were combined separately and then added slowly to the aqueous gel while stirring at moderate speed 200 rpm. The final emulsion was homogenized for 5 min with an overhead homogenizer.

In-Vitro Sun Protection Factor Measurement and Water Resistance

The substrate used for SPF measurements were "Vitro skin" from IMS Inc. (Portland, Me.) hydrated at room temperature overnight in an hermetic plastic chamber containing 200 g of a 30 wt % solution of glycerin in water (samples do not touch the liquid). The SPF measurements were obtained using the transmittance analyzer, Labsphere UV1000.

The dry Blank was a piece of hydrated Vitro-skin. With a syringe, 0.06 g of suncare product was weighed on the in-vitro skin sample. With a gloved finger, the product was evenly spread and rubbed over the surface of the In-vitro Skin for 30 seconds. Sample was air dried for 20 min, before the dry SPF measurement. A measurement of transmittance of the dry blank was performed. Then each Vitro-skin treated sample was measured at 5 different spots (the center and four corners). After the runs of the dry SPF measurement were completed, the sample was placed into the water bath for the successive 20 min immersion periods.

Water Resistance Protocol

Four 20 min immersions followed by 20 min air dry period (80 min total water immersion time) were performed. The immersion bath was a 150 mm×75 mm Pyrex round dish with 1000 ml of deionized water and a magnetic stirring bar. The water bath was stirred at 300 rpm (revolutions per minute) at room temperature (23° C.). The water resistance value in Table was the ratio of the dry SPF value to the wet SPF value, multiplied by 100.

TABLE 2

Sunscreen composition

| Components | Ex. 5 | Comp. 5 |
| --- | --- | --- |
| Carbopol 1382 | | 0.2 |
| Composition of present invention (Example 2) | 3 | |
| Silsoft 840 | | 3 |

TABLE 2-continued

Sunscreen composition

| Components | Ex. 5 | Comp. 5 |
|---|---|---|
| Avobenzone | 2.6 | 2.6 |
| Homosalate | 8.8 | 8.8 |
| Octisalate | 4.4 | 4.4 |
| Octocrylene | 8.8 | 8.8 |
| Oxybenzone | 5.3 | 5.3 |
| Water | 67 | 67 |
| Amino methyl propanol | 0 | q.s to pH 7 |

TABLE 3

SPF measurement of sunscreen formulations

| Property | Ex. 5 | Comp. 5 |
|---|---|---|
| SPF (dry) | 50 | 40 |
| % water resistance | 76 | 3.5 |

Silsoft 840 is an oil in water emulsifier sold by Momentive. The composition of the present invention showed a high water resistance compared to the comparative example.

Example 6

High Glycerin Moisturizing Creams

The composition prepared according to the present invention was combined with the glycerin and the water and stirred with a U-shape blade with a conventional overhead mixer for 1 hour. The starch was added at the end. The blend was homogenized.

| Ingredients | Wt % | | |
|---|---|---|---|
| composition prepared according to the present invention | 5 | 10 | 5 |
| glycerin | 40 | 60 | 40 |
| Starch | | | 5 |
| water | q.s. to 100 | q.s. to 100 | q.s to 100 |
| pH | 6.3 | 6.3 | 6.3 |

Example 7

Inorganic Sunscreen Paste

The composition prepared according to the present invention was combined with the glycerin and stirred with a U-shape blade with a conventional overhead mixer for 1 hour (phase A). The silicone gel (Velvesil DM), the dimethicone and Parsol TX (TiO2) were combined together with a Flakteck mixer at 2000 rpm for 2 min. The silicone/TiO2 blend were mixed with phase A (glycerin+composition of the present invention) with the Flakteck mixer for 2 min at 2000 rpm. The water was added at the end. Velvesil DM was from Momentive Performance Materials, Parsol TX was from DSM Inc,

| Ingredients | Wt % |
|---|---|
| composition prepared according to the present invention | 8 |
| Glycerin | 32 |
| Velvesil DM | 35 |
| Dimethicone 5 cp | 5 |
| Parsol TX (TiO2) | 10 |
| Water | 5 |

Example 8

High Oil Hair Cream

The composition prepared according to the present invention was combined with the water and stirred with a U-shape blade with a conventional overhead mixer for 1 hour. The pH was adjusted to pH 5 with a 10% citric solution. While stirring, the olive oil was added slowly to the aqueous gel. The final emulsion was homogenized for 5 min with an overhead homogenizer.

| Ingredients | Wt % |
|---|---|
| composition prepared according to the present invention | 2.5 |
| Olive oil | 50 |
| water | q.s. to 100 |
| pH | 5 |

Example 9

Styling Gel

The composition prepared according to the present invention was combined with the water and stirred with a U-shape blade with a conventional overhead mixer for 1 hour. PVP/VA W-735 was added to the aqueous gel, while stirring.

| Ingredients | Wt % |
|---|---|
| composition prepared according to the present invention | 5 |
| PVP/VA W-735 | 6 |
| Water | q.s. to 100 |

PVP/VA W-735 was front Ashland.

Example 10

BB cream

The composition prepared according to the present invention was combined with the water phase and stirred with a U-shape blade with a conventional overhead mixer for 1 hour to form an aqueous gel. The pigments and the oil were combined separately. The mixture of pigments and the oil was added to the aqueous gel at once and stirred for 15 min. The final emulsion was homogenized for 5 min on an overhead homogenizer.

| Ingredients | Wt % |
|---|---|
| composition prepared according to the present invention | 3 |
| Titanium dioxide and triethoxycaprylsylsilane (BTD-11S2) | 3.8 |
| Iron oxides and triethoxycaprylsylsilane (BYO-11S2) | 0.85 |
| Iron oxides and triethoxycaprylsylsilane (BRO-11S2) | 0.3 |

-continued

| Ingredients | Wt % |
|---|---|
| Iron oxides and triethoxycaprylsylsilane (BBO-11S2) | 0.1 |
| Boron nitride (Softouch CCS402) | 3 |
| Mineral oil | 20 |
| Glycerin | 5 |
| water | q.s to 100 |

Example 11

Soft Focus Moisturizing Cream

The composition prepared according to the present invention was combined with the water phase and stirred with a U-shape blade with a conventional overhead mixer for 1 hour to form an aqueous gel. The solid particles and the oil were combined separately. The mixture of pigments and the oil was added to the aqueous gel at once and stirred for 15 min. The final emulsion was homogenized for 5 min on an overhead homogenizer.

| Ingredients | Wt % |
|---|---|
| composition prepared according to the present invention | 3 |
| Boron nitride powder (Softouch CCS102) | 3.8 |
| Polymethylsilsesquioxane (Tospearl 2000B) | 0.85 |
| Mineral oil | 20 |
| Glycerin | 5 |
| water | q.s to 100 |

What is claimed is:

1. A composition comprising a crosslinked polyacrylate salt obtained by the steps of
   (a) reacting a crosslinked polyacrylic polymer and an aminosilicone copolymer in the presence of a reaction-promoting amount of water in the range of 0.2 to 0.99 wt % based on the total weight of the intermediate wax composition at a temperature range of from 90 to 120° C. for a reaction time of from 4 to 6 hours to obtain an intermediate wax composition; and
   (b) reacting the intermediate wax composition with an aqueous solution of an organic amine base solution to produce the crosslinked polyacrylate salt,
   wherein
   the crosslinked polyacrylate salt has a backbone represented by the general formula:

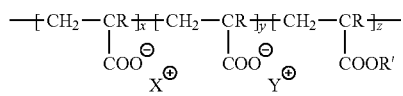

wherein
R is selected from the group consisting of hydrogen, alkyl group, aryl group, alkaryl/aralkyl groups, and cycloaliphatic groups,
R' is selected from the group consisting of alkyl group, aryl group and alkyl/aryl groups having from 1 to 30 carbon atoms,
$X^\oplus$ is a cationic amine group of the aminosilicone copolymer,
$Y^\oplus$ is a cationic amine group of the organic amine base of tromethamine, x is an integer between 50 and 20,000;
y is an integer between 50 and 20,000;
z is an integer between 0 and 5,000; and,
the ratio of x:(x+y) is between 0.02 and 0.2,
wherein
the aminosilicone copolymer is selected from the group consisting of
(i) an aminosilicone copolymer resulting from the epoxy ring opening reaction of:
$R^1R^2NH$ and

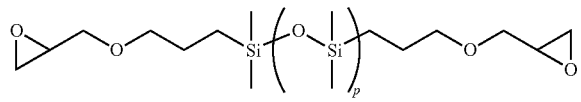

wherein
$R^1$ is $-R^3(OCH_2CH_2)_a[OCH(CH_3)CH_2]_m-$,
$R^2$ is H,
$R^3$ is $(C_nH_{2n+1})-$ where n is an integer from 1 to 30, or $(C_{n'}H_{2n'-1})-$ where n' is an integer from 2 to 30, or $(C_{n''}H_{2n''-3})-$ where n" is an integer from 4 to 30,
a is an integer from 2 to 4,
m is 0 or an integer from 1 to 100,
and
p is an integer from 2 to 1,000;
(ii) a block copolymer having the general formula of [AB]n
wherein
A is a polysiloxane group having the general formula of $[X(C_aH_{2a}O)_bR^6[(SiO(R^5)_2]_cSi(R^5)_2R^6(OC_aH_{2a})_bX]$, B is a polyalkyleneoxide group having the general formula of $[YO(C_aH_{2a}O)_dY]$, $R^5$ is an alkyl containing from 1 to 4 carbon atoms,
$R^6$ is a divalent organic moiety,
X and Y are divalent organic groups selected from a secondary or tertiary amine and a ring opened epoxide, such that when X is a ring opened epoxide, Y is an amine and vice versa,
a is independently 2 to 4,
b is independently 0 to 100,
c is 1 to 500,
d is 0 to 100,
n is an integer from 1 to 500, and
(b+d) is 1 to 100; and,
(iii) a random copolymer of C and D
wherein
C is a polysiloxane group having the general formula:

$-CR^7R^8-CR^9(OH)R^{11}-(SiR^{10}_2O)_x-SiR^{10}_2-$
$R^{11}CR^9(OH)CR^7R^8-L-$ wherein
$R^7$ is independently selected from the group consisting of hydrogen and alkyl, aryl, alkenyl, or aralkyl group containing up to 20 carbon atoms, and optionally containing an oxygen atom,
$R^8$ is independently selected from the group consisting of a bond, hydrogen and an alkyl, aryl, alkenyl, or aralkyl group containing up to 20 carbon atoms, and optionally containing an oxygen atom,
$R^9$ is independently selected from the group consisting of hydrogen, and an alkyl, aryl, alkenyl, or aralkyl group containing up to 20 carbon atoms, and optionally containing an oxygen atom, with the proviso that if $R^8$ is a chemical bond, then $R^9$ is a divalent hydrocarbon group of from 1 to 20 carbon atoms, and optionally containing an oxygen atom, that form a ring containing the chemical bond, $R^8$, $R^{10}$ is independently selected from the group consisting of hydrogen, and an alkyl, alkenyl, aryl or aralkyl group containing up to 10 carbon atoms, $R^{11}$ is a divalent hydrocarbon radical containing from 1 to 20 carbon atoms, and optionally containing an oxygen atom, L is independently a divalent linking group selected from the group consisting of $-N(R^{12}NR^{13}{}_2)-$ and

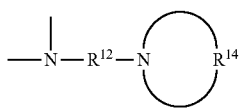

wherein
$R^{12}$ is a divalent hydrocarbon radical containing from 1 to 20 carbon atoms,
$R^{13}$ is independently hydrocarbon radical containing from 1 to 20 carbon atoms, and
$R^{14}$ is a divalent hydrocarbon group containing from 2 to 20 carbon atoms, and optionally containing an oxygen atom or an $-NR^{13}-$ group,
x is an integer from 1 to 500, and
D is a polyalkylene oxide having the general formula of $-CR^7R^8-CR^9(OH)R^{11}-O(C_aH_{2a}O)_bR^{11}C-R^9(OH)CR^7R^8$-L- wherein $R^7$, $R^8$, $R^9$, $R^{11}$, L, a and b are defined as above, wherein the obtained crosslinked polyacrylate salt has a Brookfield viscosity at 25° C. in the range of 15,000 to 50,000 cp when diluted at 3 wt % in water.

2. The composition of claim 1 wherein the reaction-promoting amount of water is in the range of 0.3 to 0.99 wt% based on the total weight of the intermediate wax composition.

3. The composition of claim 1 wherein the crosslinked polyacrylic polymer is selected from the group consisting of homopolymer of an unsaturated, polymerizable carboxylic monomer and copolymer of polymerizable carboxylic monomers.

4. The composition of claim 3, wherein the polymerizable carboxylic monomer is selected from the group consisting of acrylic acid, methacrylic acid, maleic acid, itaconic acid and maleic anhydride.

5. The composition of claim 1 wherein the reaction of step (a) further comprises the presence of a non-aqueous diluent.

6. An aqueous emulsion comprising the composition of claim 1.

7. The composition of claim 1 wherein the composition is used in a personal care composition, a cosmetic composition, a textile composition, an oil extraction composition, a coating composition, a paint composition, an agrochemical composition, a lubrication composition, a composition requiring irreversible thickening, and an emulsification composition.

8. A personal care composition comprising the composition of claim 1.

9. A hair care or skin care composition comprising the composition of claim 1.

10. A process for producing a composition containing a crosslinked polyacrylate salt, wherein the process comprising the steps of (a) reacting a crosslinked polyacrylic polymer and an aminosilicone copolymer in the presence of a reaction-promoting amount of water of 0.2 wt % to 0.99 wt % at a temperature range of from 90 to 120° C. for a reaction time of from 4 to 6 hours to obtain an intermediate wax composition; and (b) reacting the intermediate wax composition with an aqueous solution of an organic amine base solution to produce the crosslinked polyacrylate salt, wherein
the crosslinked polyacrylate salt has a backbone represented by the general formula:

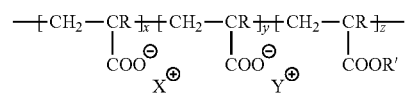

wherein
R is selected from the group consisting of hydrogen, alkyl group, aryl group, alkaryl/aralkyl groups, and cycloaliphatic groups,
R' is selected from the group consisting of alkyl group, aryl group and alkyl/aryl groups having from 1 to 30 carbon atoms,
$X^\oplus$ is a cationic amine group of the aminosilicone copolymer,
$Y^\oplus$ is a cationic amine group of the organic amine base of tromethamine,
x is an integer between 50 and 20,000;
y is an integer between 50 and 20,000;
z is an integer between 0 and 5,000; and,
the ratio of x:(x+y) is between 0.02 and 0.2,
wherein
the aminosilicone copolymer is selected from the group consisting of
(i) an aminosilicone copolymer resulting from the reaction of:
$R^1R^2NH$ and

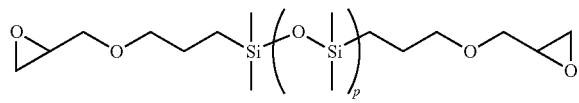

wherein
$R^1$ is $-R^3(OCH_2CH_2)_a[OCH(CH_3)CH_2]_m-$,
$R^2$ is H,
$R^3$ is $(C_nH_{2n+1})-$ where n is an integer from 1 to 30, or $(C_{n'}H_{2n'-1})-$ where n' is an integer from 2 to 30, or $(C_{n''}H_{2n''-3})-$ where n" is an integer from 4 to 30,
a is an integer from 2 to 4,
m is 0 or an integer from 1 to 100,
p is an integer from 2 to 1,000;
(ii) a block copolymer having the general formula of [AB]n
wherein
A is a polysiloxane group having the general formula of

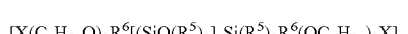

B is a polyalkyleneoxide group having the general formula of

[YO(C$_a$H$_{2a}$O)$_d$Y],

R$^5$ is an alkyl containing from 1 to 4 carbon atoms,
R$^6$ is a divalent organic moiety,
X and Y are divalent organic groups selected from a secondary or tertiary amine and a ring opened epoxide, such that when X is a ring opened epoxide, Y is an amine and vice versa,
a is independently 2 to 4,
b is independently 0 to 100,
c is 1 to 500,
d is 0 to 100, and
(b+d) is 1 to 100; and,
(iii) a random copolymer of C and D
wherein
C is a polysiloxane group having the general formula:

—CR$^7$R$^8$—CR$^9$(OH)R$^{11}$—(SiR$^{10}$$_2$O)$_x$—SiR$^{10}$$_2$—R$^{11}$CR$^9$(OH)CR$^7$R$^8$-L- wherein
R$^7$ is independently selected from the group consisting of hydrogen and alkyl, aryl, alkenyl, or aralkyl group containing up to 20 carbon atoms, and optionally containing an oxygen atom,
R$^8$ is independently selected from the group consisting of a bond, hydrogen, and an alkyl, aryl, alkenyl, or aralkyl group containing up to 20 carbon atoms, and optionally containing an oxygen atom,
R$^9$ is independently selected from the group consisting of hydrogen, and an alkyl, aryl, alkenyl, or aralkyl group containing up to 20 carbon atoms, and optionally containing an oxygen atom,
with the proviso that if R$^8$ is a chemical bond, then R$^9$ is a divalent hydrocarbon group of from 1 to 20 carbon atoms, and optionally containing an oxygen atom, that form a ring containing the chemical bond, R$^8$,
R$^{10}$ is independently selected from the group consisting of hydrogen, and an alkyl, alkenyl, aryl or aralkyl group containing up to 10 carbon atoms,
R$^{11}$ is a divalent hydrocarbon radical containing from 1 to 20 carbon atoms, and optionally containing an oxygen atom,
L is independently a divalent linking group selected from the group consisting of —N(R$^{12}$NR$^{13}$$_2$)— and

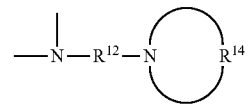

wherein
R$^{12}$ is a divalent hydrocarbon radical containing from 1 to 20 carbon atoms,
R$^{13}$ is independently hydrocarbon radical containing from 1 to 20 carbon atoms, and
R$^{14}$ is a divalent hydrocarbon group containing from 2 to 20 carbon atoms, and optionally containing an oxygen atom or an —NR$^{13}$— group,
x is an integer from 1 to 500, and
D is a polyalkylene oxide having the general formula of —CR$^7$R$^8$—CR$^9$(OH)R$^{11}$—O(C$_a$H$_{2a}$O)$_b$R$^{11}$C—R$^9$(OH)CR$^7$R$^8$-L- wherein R$^7$, R$^8$, R$^9$, R$^{11}$, L, a and b are defined as above, wherein the obtained crosslinked polyacrylate salt has a Brookfield viscosity at 25° C. in the range of 15,000 to 50,000 cp when diluted at 3 wt % in water.

11. The process of claim 10 wherein the reaction-promoting amount of water is in the range of 0.3 to 0.99 wt % based on the total weight of the intermediate wax composition.

12. A personal care composition comprising a composition made by the process of claim 10.

13. A hair care or skin care composition comprising a composition made by the process of claim 10.

14. The composition of claim 1, wherein the reaction-promoting amount of water is in the range of 0.5 to 0.99 wt % based on the total weight of the intermediate wax composition.

15. The composition of claim 1, wherein the amount of crosslinked polyacrylate salt present in the composition is from 1.46 wt. % to 48.71 wt. % based on the weight of the composition.

16. The composition of claim 1, wherein the amount of crosslinked polyacrylate salt obtained by the process is from 46.12 wt. % to 48.71 wt. % based on the weight of the composition.

* * * * *